(12) United States Patent
Tobler et al.

(10) Patent No.: US 8,551,912 B2
(45) Date of Patent: Oct. 8, 2013

(54) FUNGICIDAL COMPOSITIONS

(75) Inventors: Hans Tobler, Basel (CH); Harald Walter, Stein (CH); Ulrich Johannes Haas, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 695 days.

(21) Appl. No.: 12/597,221

(22) PCT Filed: Apr. 23, 2008

(86) PCT No.: PCT/EP2008/003279
§ 371 (c)(1),
(2), (4) Date: Mar. 10, 2010

(87) PCT Pub. No.: WO2008/131901
PCT Pub. Date: Nov. 6, 2008

(65) Prior Publication Data
US 2010/0216640 A1 Aug. 26, 2010

(30) Foreign Application Priority Data
Apr. 25, 2007 (EP) ..................................... 07008370

(51) Int. Cl.
*A01N 43/40* (2006.01)
*A01N 43/54* (2006.01)
*A01N 43/56* (2006.01)
*A01N 43/88* (2006.01)
*A01N 37/44* (2006.01)
*A01N 37/50* (2006.01)
*A01N 47/10* (2006.01)
*A01P 3/00* (2006.01)

(52) U.S. Cl.
USPC ........ 504/100; 504/206; 514/229.2; 514/269; 514/345; 514/407; 514/539

(58) Field of Classification Search
USPC .............. 514/269, 406, 229.2, 345, 407, 539; 504/100, 206
See application file for complete search history.

(56) References Cited

U.S. PATENT DOCUMENTS 6,444,693 B1   9/2002   Wachendorff-Neumann et al.

FOREIGN PATENT DOCUMENTS

| RU | 2237996 | 10/2004 |
|----|---------|---------|
| WO | 2004035589 | 4/2004 |
| WO | 2006037632 | 4/2006 |
| WO | 2006/108552 | 10/2006 |
| WO | 2007/009661 | 1/2007 |
| WO | WO 2007/048556 | * 5/2007 |

OTHER PUBLICATIONS

CABA abstract 1997:75026 (1997).*
Godoy, C.V. et al., "Protective, curative and eradicative effects of fungicides to control soybean rust caused by Phakopsora pachyrhizi, in greenhouse," Fitopatologia Brasileira, vol. 29(1), pp. 97-101 (2004).*
CABA abstract 2005:80841 (2005).*

* cited by examiner

*Primary Examiner* — John Pak
(74) *Attorney, Agent, or Firm* — R. Kody Jones

(57) ABSTRACT

A composition suitable for control of diseases caused by phytopathogens comprising (A) a compound of Formula (I) wherein $R_1$ is difluoromethyl or trifluoromethyl and X is chloro, fluoro or bromo; and (B) at least one compound selected from compounds known for their fungicidal activity; and a method of controlling diseases on useful plants, especially rust diseases on soybean plants.

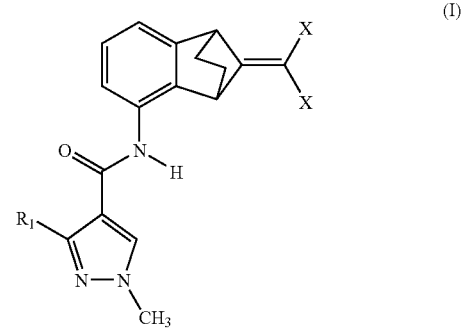

(I)

12 Claims, No Drawings

FUNGICIDAL COMPOSITIONS

This application is a 371 of International Application No. PCT/EP2008/003279 filed Apr. 23, 2008, which claims priority to EP 07008370.4 filed Apr. 25, 2007, the contents of which are incorporated herein by reference.

The present invention relates to novel fungicidal compositions suitable for control of diseases caused by phytopathogens, especially phytopathogenic fungi and to a method of controlling diseases on useful plants, especially rust diseases on soybean plants.

It is known from WO 04/35589 and WO 06/37632 that certain tricyclic amine derivatives and mixtures comprising said amine derivatives have biological activity against phytopathogenic fungi. On the other hand various fungicidal compounds of different chemical classes are widely known as plant fungicides for application in various crops of cultivated plants. However, crop tolerance and activity against phytopathogenic plant fungi do not always satisfy the needs of agricultural practice in many incidents and aspects. For example, in the past in the most important regions for soybean cultures no economically significant phytopathogens were known. However, recently there has been an increase in severe rust infections of soybean crops in South America by the harmful fungus *Phakopsora pachyrhizi* resulting in considerable yield losses. Most customary fungicides are unsuitable for controlling rust in soybeans or their action against *Phakopsora pachyrhizi* is unsatisfactory.

Out of the above-mentioned needs of agricultural practice for increased crop tolerance and/or increased activity against phytopathogenic fungi, such as *Phakopsora pachyrhizi*, there is therefore proposed in accordance with the present invention a novel composition suitable for control of diseases caused by phytopathogens comprising a composition suitable for control of diseases caused by phytopathogens comprising
(A) a compound of formula I

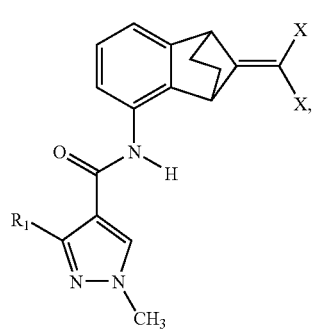

wherein $R_1$ is difluoromethyl or trifluoromethyl and X is chloro, fluoro or bromo; and
(B) at least one compound selected from the group consisting of
(B1) a strobilurin fungicide,
(B2) an azole fungicide,
(B3) a morpholine fungicide,
(B4) an anilinopyrimidine fungicide,
(B5) a fungicide selected from the group consisting of
anilazine, arsenates, benalaxyl, benalaxyl-M, benodanil, benomyl, benthiavalicarb, benthiavalicarb-isopropyl, biphenyl, bitertanol, blasticidin-S, bordeaux mixture, boscalid, bupirimate, cadmium chloride, captafol, captan, carbendazim, carbon disulfide, carboxin, carpropamid, cedar leaf oil, chinomethionat, chlorine, chloroneb, chlorothalonil, chlozolinate, cinnamaldehyde, copper, copper ammoniumcarbonate, copper hydroxide, copper octanoate, copper oleate, copper sulphate, cyazofamid, cycloheximide, cymoxanil, dichlofluanid, dichlone, dichloropropene, diclocymet, diclomezine, dicloran, diethofencarb, diflumetorim, dimethirimol, dimethomorph, dinocap, dithianon, dodine, edifenphos, ethaboxam, ethirimol, etridiazole, famoxadone, fenamidone, fenaminosulf, fenamiphos, fenarimol, fenfuram, fenhexamid, fenoxanil, fenpiclonil, fentin acetate, fentin chloride, fentin hydroxide, ferbam, ferimzone, fluazinam, fludioxonil, flusulfamide, flusulfamide, flutolanil, folpet, formaldehyde, fosetyl-aluminium, fthalide, fuberidazole, furalaxyl, furametpyr, flyodin, fuazatine, hexachlorobenzene, hymexazole, iminoctadine, iodocarb, iprobenfos, iprodione, iprovalicarb, isoprothiolane, kasugamycin, mancozeb, maneb, manganous dimethyldithiocarbamate, mefenoxam, mepronil, mercuric chloride, mercury, metalaxyl, methasulfocarb, metiram, metrafenone, nabam, neem oil (hydrophobic extract), nuarimol, octhilinone, ofurace, oxadixyl, oxine copper, oxolinic acid, oxycarboxin, oxytetracycline, paclobutrazole, paraffin oil, paraformaldehyde, pencycuron, pentachloronitrobenzene, pentachlorophenol, penthiopyrad, perfurazoate, phosphoric acid, polyoxin, polyoxin D zinc salt, potassium bicarbonate, probenazole, procymidone, propamocarb, propineb, proquinazid, prothiocarb, pyrazophos, pyrifenox, pyroquilon, quinoxyfen, quintozene, silthiofam, sodium bicarbonate, sodium diacetate, sodium propionate, streptomycin, sulphur, TCMTB, tecloftalam, tecnazene, thiabendazole, thifluzamide, thiophanate, thiophanate-methyl, thiram, tolclofos-methyl, tolyfluanid, triazoxide, trichoderma harzianum, tricyclazole, triforine, triphenyltin hydroxide, validamycin, vinclozolin, zineb, ziram, zoxamide, 1,1-bis(4-chlorophenyl)-2-ethoxyethanol, 2,4-dichlorophenyl benzenesulfonate, 2-fluoro-N-methyl-N-1-naphthylacetamide, 4-chlorophenyl phenyl sulfone,
a compound of formula B-5.1

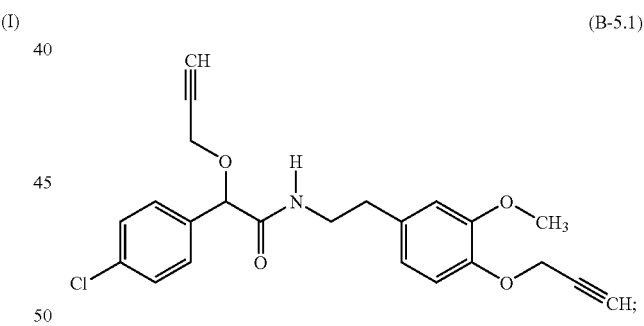

a compound of formula B-5.2

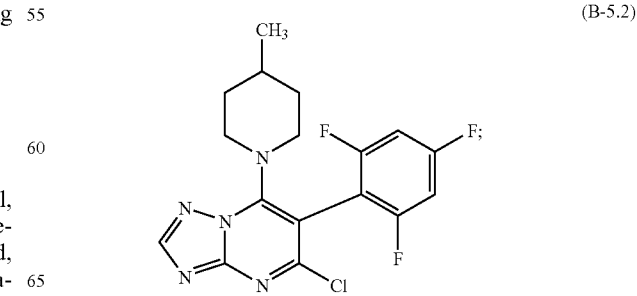

a compound of formula B-5.3

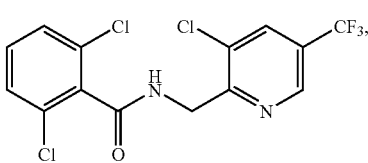

a compound of formula B-5.4

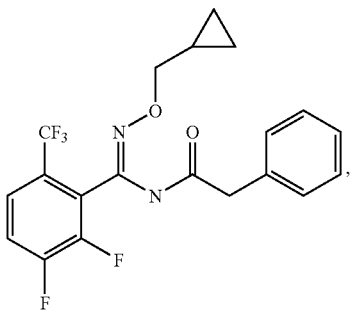

a compound of formula B-5.5

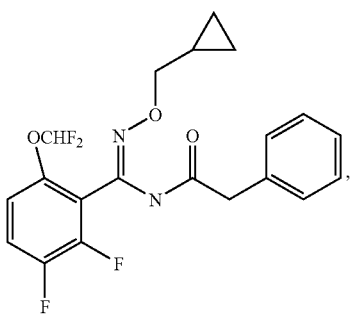

a compound of formula B-5.6

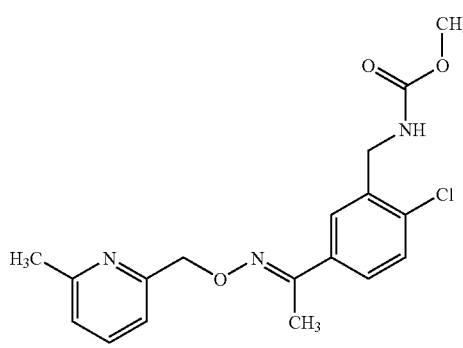

a compound of formula B-5.7

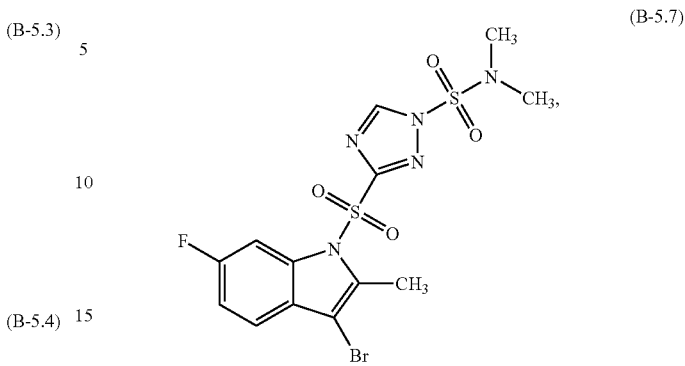

3-difluoromethyl-1-methyl-1H-pyrazole-4-carboxylic acid (2-bicyclopropyl-2-yl-phenyl)-amide (compound B-5.8), 3-difluoromethyl-1-methyl-1H-pyrazole-4-carboxylic acid (9-isopropyp-1,2,3,4-tetrahydro-1,4-methano-naphthalen-5-yl)-amide (compound B-5.9), 1,3-dimethyl-5-fluoro-1H-pyrazole-4-carboxylic acid [2-(1,3-dimethylbutyl)phenyl]-amide (compound B-5.10), 3-difluoromethyl-1-methyl-1H-pyrazole-4-carboxylic acid (3',4'-dichloro-5-fluoro-1,1'-biphenyl-2-yl)-amide (compound B-5.11), N-{2-[3-chloro-5-(trifluoromethyl)pyridin-2-yl]ethyl}-2-(trifluoromethyl) benzamid (compound B-5.12), 3-difluoromethyl-1-methyl-1H-pyrazole-4-carboxylic acid N-[2-(1,1,2,2-tetrafluoroethoxy)phenyl]-amide (compound B-5.13), 3-difluoromethyl-1-methyl-1H-pyrazole-4-carboxylic acid N-[2-(1,1,2,3,3,3-hexafluoropropoxy)phenyl]-amide (compound B-5.14), 3-difluoromethyl-1-methyl-1H-pyrazole-4-carboxylic acid N-[2-(2-chloro-1,1,2-trifluoroethoxy)phenyl]-amide (compound B-5.15), 3-difluoromethyl-1-methyl-1H-pyrazole-4-carboxylic acid N-(4'-trifluoromethyl-biphen-2-yl)-amide (compound B-5.16), 3-difluoromethyl-1-methyl-1H-pyrazole-4-carboxylic acid N-(2'-trifluoromethyl-biphen-2-yl)-amide (compound B-5.17) and 3-difluoromethyl-1-methyl-1H-pyrazole-4-carboxylic acid N-(2'-trifluoromethyl-biphen-2-yl)-amide (compound B-5.18); (B6) a plant-bioregulator selected from the group consisting of
acibenzolar-S-methyl, chlormequat chloride, ethephon, mepiquat chloride and trinexapc-ethyl;
(B7) an insecticide selected from the group consisting of abamectin, clothianidin, emamectin benzoate, imidacloprid, tefluthrin, thiamethoxam,
and a compound of formula IV

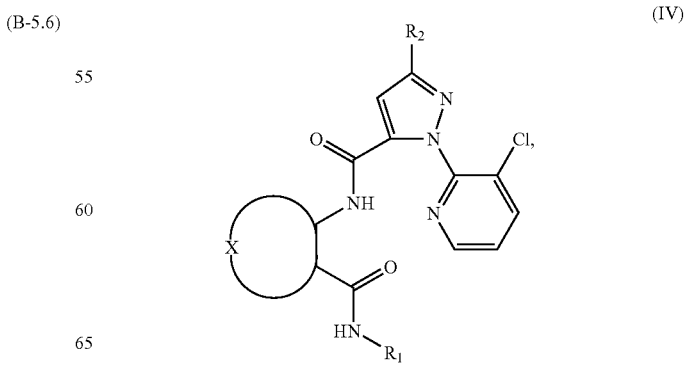

wherein X is a bivalent group selected from

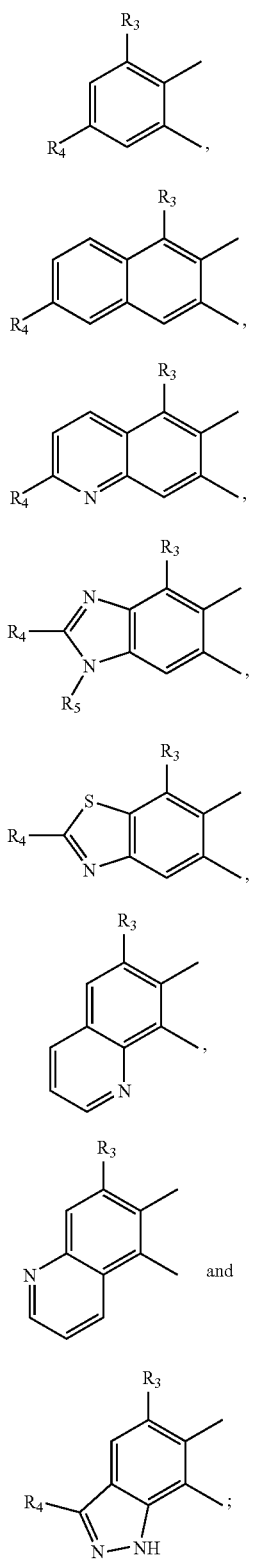

wherein
a) $R_1$ is cyclopropyl substituted by cyclopropyl at the 1-position, $R_2$ is bromine, $R_3$ is methyl, $R_4$ is CN and X is $X_1$;
b) $R_1$ is methyl substituted by cyclopropyl, $R_2$ is $CF_3$, $R_3$ is methyl, $R_4$ is Cl and X is $X_1$;
c) $R_1$ is cyclopropyl substituted by cyclopropyl at the 1-position, $R_2$ is $CF_3$, $R_3$ is methyl, $R_4$ is Cl and X is $X_1$;
d) $R_1$ is cyclopropyl substituted by cyclopropyl at the 1-position, $R_2$ is $CF_3$, $R_3$ is methyl, $R_4$ is CN and X is $X_1$;
e) $R_1$ is cyclopropyl substituted by cyclopropyl at the 1-position, $R_2$ is $OCH_2CF_3$, $R_3$ is methyl, $R_4$ is CN and X is $X_1$;
f) $R_1$ is isopropyl, $R_2$ is methoxy; $R_3$ is methyl, $R_4$ is hydrogen and X is $X_8$;
g) $R_1$ is isopropyl, $R_2$ is trifluoromethyl, $R_3$ is chlorine, $R_4$ is hydrogen and X is $X_8$;
h) $R_1$ is isopropyl, $R_2$ is trifluoromethyl, $R_3$ is methyl, $R_4$ is hydrogen and X is $X_8$;
i) $R_1$ is methyl, $R_2$ is bromine, $R_3$ is methyl, $R_4$ is CN and X is $X_1$;
j) $R_1$ is methyl, $R_2$ is bromine, $R_3$ is methyl, $R_4$ is Cl and X is $X_1$;
and (B8) glyphosate, a compound of formula V

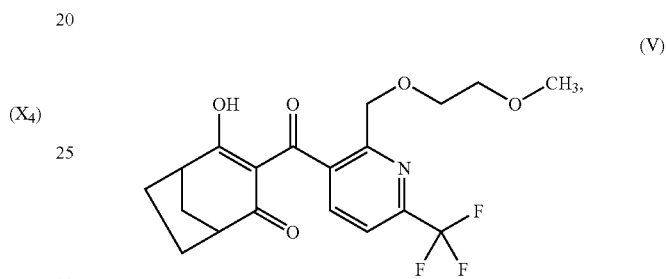

fomesafen, and (B9) a racemic compound of formula VIa (syn)

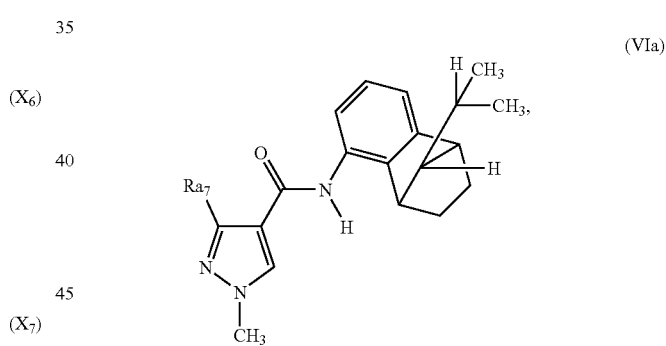

wherein $Ra_7$ is trifluoromethyl or difluoromethyl; a racemic mixture of formula VIb (anti)

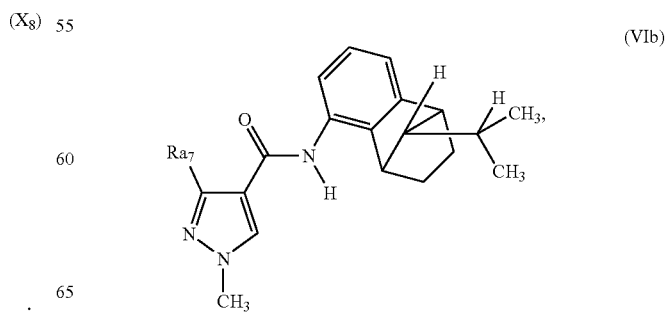

wherein Ra$_7$ is trifluoromethyl or difluoromethyl; a compound of formula VIc (VIc)

which is an epimeric mixture of racemic compounds of formulae F-10 (syn) and F-11 (anti), wherein the ratio from racemic compounds of formula F-10 (syn) to racemic compounds of formula F-11 (anti) is from 1000:1 to 1:1000 and wherein Ra$_7$ is trifluoromethyl or difluoromethyl.

Preferred compositions comprising (A) a compound of formula I (I)

wherein R$_1$ is difluoromethyl or trifluoromethyl and X is chloro, fluoro or bromo; and
(B) a compound selected from the group consisting of
(B1) a strobilurin fungicide, (B2) an azole fungicide, (B3) a morpholine fungicide, (B4) an anilinopyrimidine fungicide, (B5) a fungicide selected from the group consisting of anilazine (878), arsenates, benalaxyl (56), benalaxyl-M, benodanil (896), benomyl (62), benthiavalicarb, benthiavalicarb-isopropyl (68), biphenyl (81), bitertanol (84), blasticidin-S (85), bordeaux mixture (87), boscalid (88), bupirimate (98), cadmium chloride, captafol (113), captan (114), carbendazim (116), carbon disulfide (945), carboxin (120), carpropamid (122), cedar leaf oil, chinomethionat (126), chlorine, chloroneb (139), chlorothalonil (142), chlozolinate (149), cinnamaldehyde, copper, copper ammoniumcarbonate, copper hydroxide (169), copper octanoate (170), copper oleate, copper sulphate (87), cyazofamid (185), cycloheximide (1022), cymoxanil (200), dichlofluanid (230), dichlone (1052), dichloropropene (233), diclocymet (237), diclomezine (239), dicloran (240), diethofencarb (245), diflumetorim (253), dimethirimol (1082), dimethomorph (263), dinocap (270), dithianon (279), dodine (289), edifenphos (290), ethaboxam (304), ethirimol (1133), etridiazole (321), famoxadone (322), fenamidone (325), fenaminosulf (1144), fenamiphos (326), fenarimol (327), fenfuram (333), fenhexamid (334), fenoxanil (338), fenpiclonil (341), fentin acetate (347), fentin chloride, fentin hydroxide (347), ferbam (350), ferimzone (351), fluazinam (363), fludioxonil (368), flusulfamide (394), flutolanil (396), folpet (400), formaldehyde (404), fosetyl-aluminium (407), fthalide (643), fuberidazole (419), furalaxyl (410), furametpyr (411), flyodin (1205), fuazatine (422), hexachlorobenzene (434), hymexazole, iminoctadine (459), iodocarb (3-Iodo-2-propynyl butyl carbamate), iprobenfos (IBP) (469), iprodione (470), iprovalicarb (471), isoprothiolane (474), kasugamycin (483), mancozeb (496), maneb (497), manganous dimethyldithiocarbamate, mefenoxam (Metalaxyl-M) (517), mepronil (510), mercuric chloride (511), mercury, metalaxyl (516), methasulfocarb (528), metiram (546), metrafenone, nabam (566), neem oil (hydrophobic extract), nuarimol (587), octhilinone (590), ofurace (592), oxadixyl (601), oxine copper (605), oxolinic acid (606), oxycarboxin (608), oxytetracycline (611), paclobutrazole (612), paraffin oil (628), paraformaldehyde, pencycuron (620), pentachloronitrobenzene (716), pentachlorophenol (623), penthiopyrad, perfurazoate, phosphoric acid, polyoxin (654), polyoxin D zinc salt (654), potassium bicarbonate, probenazole (658), procymidone (660), propamocarb (668), propineb (676), proquinazid (682), prothiocarb (1361), pyrazophos (693), pyrifenox (703), pyroquilon (710), quinoxyfen (715), quintozene (PCNB) (716), silthiofam (729), sodium bicarbonate, sodium diacetate, sodium propionate, streptomycin (744), sulphur (754), TCMTB, tecloftalam, tecnazene (TCNB) (767), thiabendazole (790), thifluzamide (796), thiophanate (1435), thiophanate-methyl (802), thiram (804), tolclofos-methyl (808), tolylfluanid (810), triazoxide (821), trichoderma harzianum (825), tricyclazole (828), triforine (838), triphenyltin hydroxide (347), validamycin (846), vinclozolin (849), zineb (855), ziram (856), zoxamide (857), 1,1-bis(4-chlorophenyl)-2-ethoxyethanol (IUPAC-Name) (910), 2,4-dichlorophenyl benzenesulfonate (IUPAC-/Chemical Abstracts-Name) (1059), 2-fluoro-N-methyl-N-1-naphthylacetamide (IUPAC-Name) (1295), 4-chlorophenyl phenyl sulfone (IUPAC-Name) (981), a compound of formula B-5.1

(B-5.1)

a compound of formula B-5.2

(B-5.2)

a compound of formula B-5.3

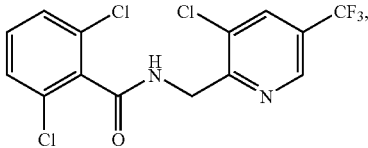
(B-5.3)

a compound of formula B-5.4

(B-5.4)

a compound of formula B-5.5

(B-5.5)

a compound of formula B-5.6

(B-5.6)

a compound of formula B-5.7

(B-5.7)

3-difluoromethyl-1-methyl-1H-pyrazole-4-carboxylic acid (2-bicyclopropyl-2-yl-phenyl)-amide (compound B-5.8), 3-difluoromethyl-1-methyl-1H-pyrazole-4-carboxylic acid (9-isopropyp-1,2,3,4-tetrahydro-1,4-methano-naphthalen-5-yl)-amide (compound B-5.9), 1,3-dimethyl-5-fluoro-1H-pyrazole-4-carboxylic acid [2-(1,3-dimethylbutyl)phenyl]-amide (compound B-5.10), 3-difluoromethyl-1-methyl-1H-pyrazole-4-carboxylic acid (3',4'-dichloro-5-fluoro-1,1'-biphenyl-2-yl)-amide (compound B-5.11), N-{2-[3-chloro-5-(trifluoromethyl)pyridin-2-yl]ethyl}-2-(trifluoromethyl) benzamid (compound B-5.12), 3-difluoromethyl-1-methyl-1H-pyrazole-4-carboxylic acid N-[2-(1,1,2,2-tetrafluoroethoxy)phenyl]-amide (compound B-5.13), 3-difluoromethyl-1-methyl-1H-pyrazole-4-carboxylic acid N-[2-(1,1,2,3,3,3-hexafluoropropoxy)phenyl]-amide (compound B-5.14), 3-difluoromethyl-1-methyl-1H-pyrazole-4-carboxylic acid N-[2-(2-chloro-1,1,2-trifluoroethoxy)phenyl]-amide (compound B-5.15), 3-difluoromethyl-1-methyl-1H-pyrazole-4-carboxylic acid N-(4'-trifluoromethyl-biphen-2-yl)-amide (compound B-5.16), 3-difluoromethyl-1-methyl-1H-pyrazole-4-carboxylic acid N-(2'-trifluoromethyl-biphen-2-yl)-amide (compound B-5.17) and 3-difluoromethyl-1-methyl-1H-pyrazole-4-carboxylic acid N-(2'-trifluoromethyl-biphen-2-yl)-amide (compound B-5.18);

(B6) a plant-bioregulator selected from the group consisting of
acibenzolar-5-methyl (6), chlormequat chloride (137), ethephon (307), mepiquat chloride (509) and trinexapc-ethyl (841);

(B7) an insecticide selected from the group consisting of
abamectin (1), clothianidin (165), emamectin benzoate (291), imidacloprid (458), tefluthrin (769), thiamethoxam (792), a compound of formula B-7.1

(B-7.1)

and a compound of formula B-7.2;

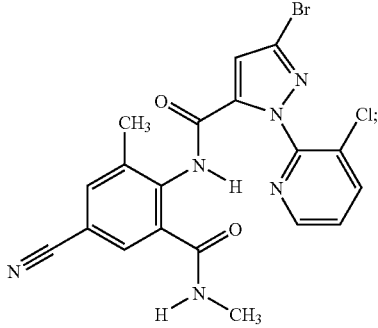
(B-7.2)

and (B8) glyphosate (419).

It has been found that the use of component (B) in combination with component (A) surprisingly and substantially enhance the effectiveness of the latter against fungi, and vice versa. Additionally, the method of the invention is effective against a wider spectrum of such fungi that can be combated with the active ingredients of this method, when used solely.

A further aspect of the present invention is a method of controlling diseases on useful plants or on propagation material thereof caused by phytopathogens, which comprises applying to the useful plants, the locus thereof or propagation material thereof a composition according to the invention. Preferred is a method, which comprises applying to the useful plants or to the locus thereof a composition according to the invention, more preferably to the useful plants. Further preferred is a method, which comprises applying to the propagation material of the useful plants a composition according to the invention.

The compounds of formula I occur in two different stereoisomers, which are described as the single enantiomers of formulae $I_I$ and $I_{II}$:

$I_I$ $I_{II}$

The invention covers all such stereoisomers and mixtures thereof in any ratio. According to the invention "racemic compound of formula (I)" means a racemic mixture of compounds of formula $I_I$ and $I_{II}$.

A preferred embodiment of the invention is represented by those compositions which comprise as component A) a compound of formula (I), wherein $R_1$ is difluoromethyl. Further preferred compounds of formula (I) are: 3-difluoromethyl-1-methyl-1H-pyrazole-4-carboxylic acid (9-dichloromethylidene-benzonorbornene-5-yl)amide (compound A-1.1); 3-difluoromethyl-1-methyl-1H-pyrazole-4-carboxylic acid (9-difluoromethylidene-benzonorbornene-5-yl)amide (compound A-1.2); and 3-difluoromethyl-1-methyl-1H-pyrazole-4-carboxylic acid (9-dibromomethylidene-benzonorbornene-5-yl)amide (compound A-1.3).

The designation of substituent X as chloro, fluoro or bromo means that both substituents X have the same meanings.

A preferred embodiment of the invention is represented by those compositions which comprise as component A) a compound of formula (I), wherein $R_1$ is trifluoromethyl. Further preferred compounds of formula (I) are:
1-methyl-3-trifluoromethyl-1H-pyrazole-4-carboxylic acid (9-dichloromethylidene-benzonorbornene-5-yl)amide (compound A-1.4);
1-methyl-3-trifluoromethyl-1H-pyrazole-4-carboxylic acid (9-difluoromethylidene-benzonorbornene-5-yl)amide (compound A-1.5); and
1-methyl-3-trifluoromethyl-1H-pyrazole-4-carboxylic acid (9-dibromomethylidene-benzonorbornene-5-yl)amide (compound A-1.6).

A further preferred embodiment of the invention is represented by those compositions which comprise as component B) a compound selected from azoxystrobin, picoxystrobin, fludioxonil, fenpropidin, difenoconazole, cyprodinil, mandipropamid, chlorothalonil, cyproconazole, epoxiconazole, propiconazole and epoxiconazole.

Especially preferred compositions according to the invention comprise as component (A) a compound selected from 3-difluoromethyl-1-methyl-1H-pyrazole-4-carboxylic acid (9-dichloromethylidene-benzonorbornene-5-yl)amide (compound A-1.1) and 3-difluoromethyl-1-methyl-1H-pyrazole-4-carboxylic acid (9-difluoromethylidene-benzonorbornene-5-yl)amide (compound A-1.2), and as component (B) a compound selected from azoxystrobin, picoxystrobin, bixafen, fludioxonil, fenpropidin, fenpropimorph, fluopyram, difenoconazole, tebuconazole, ipconazole, cyprodinil, mandipropamid, chlorothalonil, cyproconazole, prothioconazole, propiconazole and epoxiconazole.

Further especially preferred compositions according to the invention comprise as component (A) the compound 3-difluoromethyl-1-methyl-1H-pyrazole-4-carboxylic acid (9-dichloromethylidene-benzonorbornene-5-yl)amide (compound A-1.1) and as component (B) a compound selected from azoxystrobin, picoxystrobin, bixafen, fludioxonil, fenpropidin, difenoconazole, cyprodinil, mandipropamid, chlorothalonil, propiconazole, cyproconazole and epoxiconazole.

Further especially preferred compositions according to the invention comprise as component (A) the compound 3-difluoromethyl-1-methyl-1H-pyrazole-4-carboxylic acid (9-difluoromethylidene-benzonorbornene-5-yl)amide (compound A-1.2) and as component (B) a compound selected from azoxystrobin, picoxystrobin, fludioxonil, fenpropidin, fenpropimorph, fluopyram, difenoconazole, ipconazole, prothioconazole, tebuconazole, cyprodinil, chlorothalonil, epoxiconazole, propiconazole, cyproconazole, and epoxiconazole.

The compounds of formula (I) may be prepared as described below with reference to reaction Schemes 1 to 3.

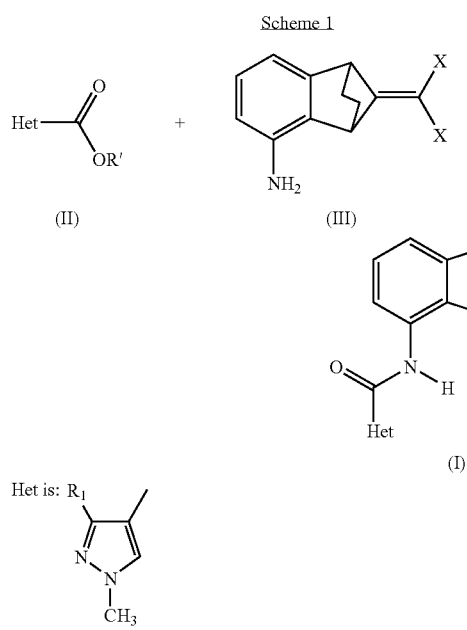

As shown in Scheme 1, a compound of formula (I), where $R_1$ and X are as defined above, may be synthesized by reacting a compound of formula (II), $R_1$ is as defined above and R' is $C_{1-5}$ alkyl, with an aniline of formula (III), where X is as defined above, in the presence of $NaN(TMS)_2$ at $-10°$ C. to ambient temperature, preferably in dry THF, as described by J. Wang et al. *Synlett*, 2001, 1485.

Alternatively, as shown in Scheme 2, a compound of formula (I), where Het is as defined in scheme 1, $R_1$ and X are as defined above, may be prepared by reacting a compound of formula (II'), where Het is as defined above, with an aniline of formula (III), where X is as defined above, in the presence of an activating agent, such as BOP—Cl (bis-(2-oxo-3-oxazolidinyl)-phosphinic acid), and two equivalents of a base, such as triethylamine, in a solvent, such as dichloromethane (as described, for example, by J. Cabré at al, Synthesis 1984, 413) or by reacting a compound of formula (II"), where Het is as defined above and Q is chloro, fluoro or bromo, with an aniline of formula (III), where X is as defined above, in the presence of one equivalent of a base, such as triethylamine or sodium or potassium carbonate or bicarbonate, in a solvent, such as dichloromethane, ethyl acetate or N,N-dimethylformamide, preferably at $-10$ to $30°$ C. The compound of formula (II") is obtained from a compound of formula (II') by treatment with a halogenating agent such as thionyl chloride, thionyl bromide, oxalyl chloride, phosgene, $SF_4/HF$, DAST ((diethylamino)sulphur trifluoride), or Deoxo-Fluor® ([bis(2-methoxyethyl)amino]sulphur trifluoride) in a solvent such as toluene, dichloromethane or acetonitrile.

The compounds (II) and (II') are generally known compounds and may be prepared as described in the chemical literature or obtained from commercial sources. The compound (III) is a novel compound and may be prepared as described with reference to Scheme 3.

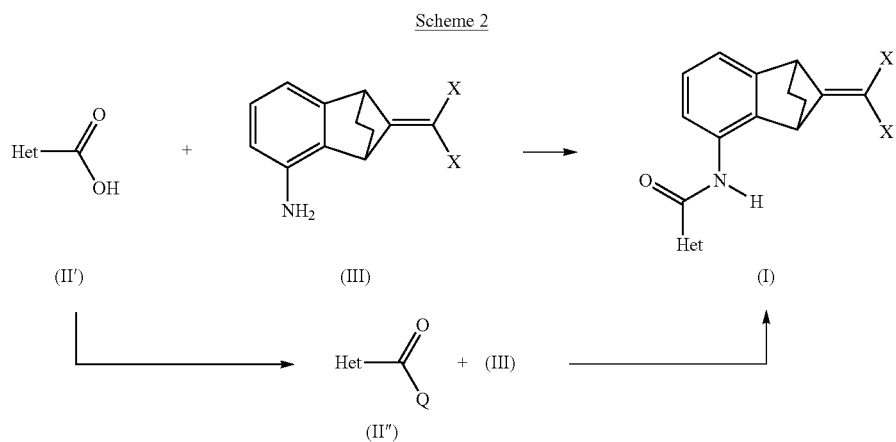

Scheme 3

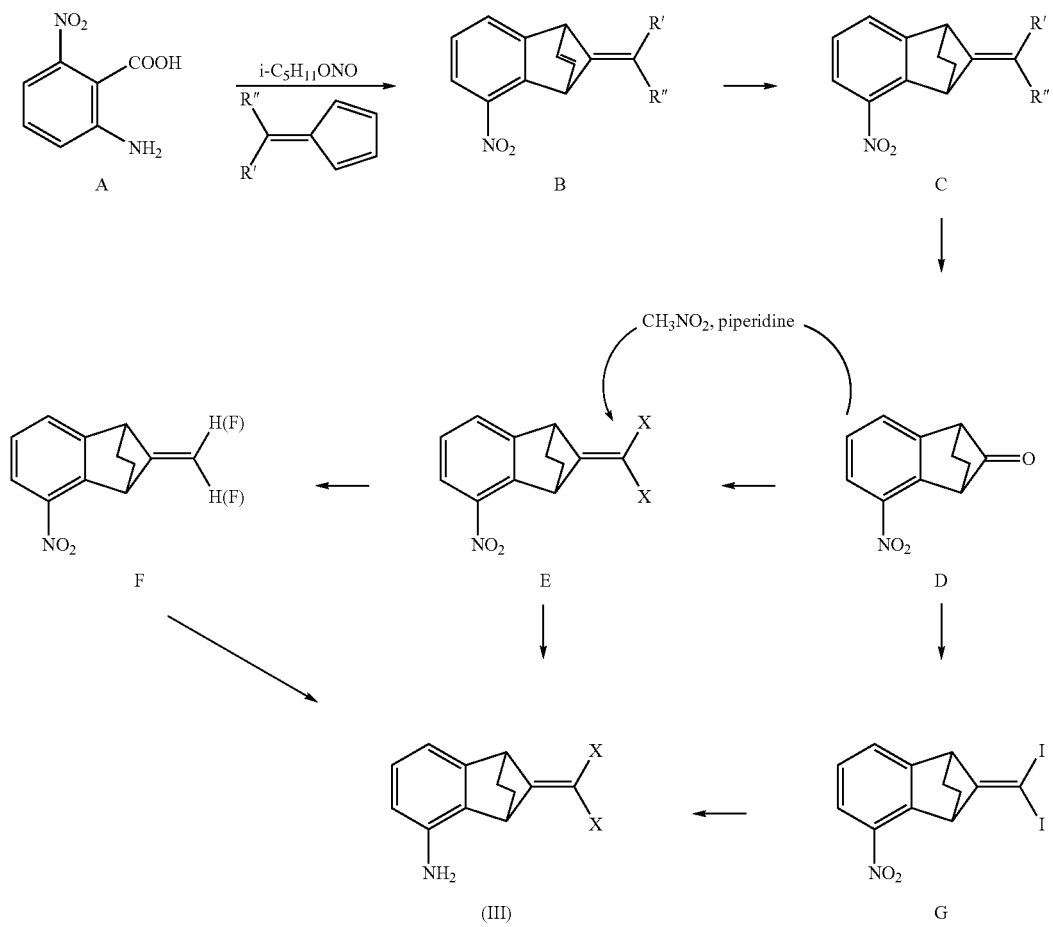

As shown in Scheme 3, the compound of formula (III) may be prepared by a Bechamp reduction or by other established methods, for example, by selective catalytic hydrogenation, of the nitro-compounds (E), (F) and (G).

The 9-dihalomethylidene-5-nitro-benzonorbornenes (E), where X is chloro, bromo or fluoro, may be obtained by the Wittig olefination of the ketones (D) with in situ generated dihalomethylidene phosphoranes $R'''_3P=C(R^4)R^5$, where $R'''$ is triphenyl, tri $C_{1-4}$ alkyl or tridimethylamine and X is halo, according to or by analogy with the procedures described by H-D. Martin et al, *Chem. Ber.* 118, 2514 (1985), S. Hayashi et al, *Chem. Lett.* 1979, 983, or M. Suda, *Tetrahedron Letters*, 22, 1421 (1981).

Compounds of formula (I) may be obtained as described in examples H1 to H7.

EXAMPLE 1

This Example illustrates the preparation of 1-methyl-3-trifluoromethyl-1H-pyrazole-4-carboxylic acid (9-dichloromethylidene-benzonorbornene-5-yl)amide (compound A-1.4):

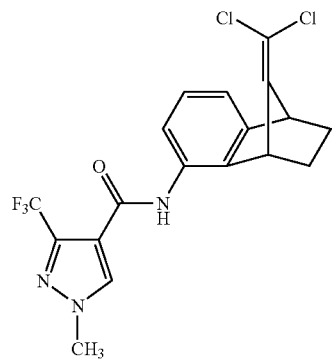 [SMILES: Cn1cc(C(=O)Nc2cccc3c2C2CCC3C2=C(Cl)Cl)c(C(F)(F)F)n1]

9-Dichloromethylene-5-amino-benzonorbornene (175 mg, 0.729 mmol, prepared as described in Example 6) in dichloromethane (10 ml) was reacted with 1-methyl-3-trifluoromethyl-1H-pyrazole-carboxylic acid (170 mg, 0.874 mmol, 1.2 eq.) in the presence of bis-(2-oxo-3-oxazolidinyl)-phosphinic acid chloride (278 mg, 1.09 mmol, 1.5 eq.) and triethylamine (184 mg, 1.821 mmol, 2.5 eq.) at ambient temperature under stirring for 23 hours. The reaction mixture was extracted with saturated sodium bicarbonate solution and saturated brine, dried over Na$_2$SO$_4$ and purified on silica gel in ethyl acetate-hexane-(1:1). 210 mg (69% of theory) of 1-methyl-3-trifluoromethyl-1H-pyrazole-4-carboxylic acid (9-dichloromethylidene-benzonorbornene-5-yl)amide (compound A-1.4, m.p. 179-181° C.) was obtained.

EXAMPLE 2

This Example illustrates the preparation of 9-(3-pentylidene)-5-nitro-benzonorbornadiene:

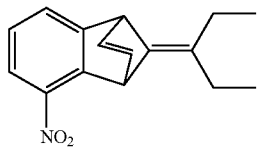 [SMILES: CCC(CC)=C1C2C=CC1c1c2cccc1[N+](=O)[O-]]

To a well stirred solution of isopentylnitrite (2.31 ml, 1.3 eq.) in dimethoxyethane (50 ml) at 58° C. a mixture of 6-nitroanthranilic acid (2.76 g, 1 eq.) and 6,6-diethylfulvene (6.45 g of 79% purity, 2.5 eq.) dissolved in 25 ml dimethoxyethane was added dropwise within 8 minutes whilst the temperature rose to 67° C. After 30 minutes the dark reaction mixture was evaporated and purified on silica gel in hexane-ethyl acetate-(20:1) to give 3.02 g (78%) of the desired product as an oil that solidified at room temperature (m.p. 60-61° C.).

EXAMPLE 3

This Example illustrates the preparation of 9-(3-pentylidene)-5-nitro-benzonorbornene:

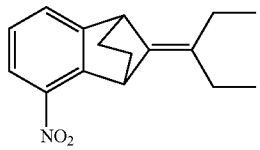

9-(3-pentylidene)-5-nitro-benzonorbornadiene (7.97 g prepared as described in Example 2) in THF (70 ml) was hydrogenated at 20° C. in the presence of Rh(PPh$_3$)$_3$Cl (Wilkinson's catalyst; 0.8 g). The reaction ceased after uptake of one equivalent of hydrogen. Evaporation and filtration of the crude on silica gel in ethyl acetate-hexane-(100:2) gave the desired product as an oil (7.90 g) that solidified on standing at room temperature (m.p. 69-56° C.).

EXAMPLE 4

This Example illustrates the preparation of 9-Oxo-5-nitro-benzonorbornene

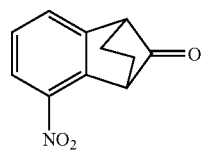 [SMILES: O=C1C2CCC1c1c2cccc1[N+](=O)[O-]]

9-(3-pentylidene)-5-nitro-benzonorbornene (7.0 g, 27.2 mmol; prepared as described in Example 3) dissolved in dichloromethane (300 ml) and methanol (5 ml) was ozonized (2.8 l O$_2$/min, 100 Watt, corresponding to 9.7 g O$_3$/h) at −70° C. until a persistent blue colour was observed (after approximately 15 minutes). The reaction mixture was flushed with nitrogen gas. Triphenylphosphine (8.4 g, 32.03 mmol, 1.18 eq.) was added and the temperature was allowed to warm up to 20-25° C. After evaporation of the solvent the residue was purified on silica gel in hexane-EtOAc-3:1 to give 5.2 g of Compound 36.01 (m.p. 112-114° C.).

EXAMPLE 5

This Example illustrates the preparation of 9-difluoromethylidene-5-nitro-benzonorbornene

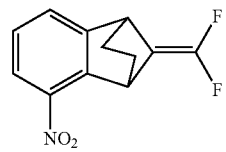

To a solution of dibromodifluoromethane (6.30 g, 30 mmol) at 0° C. in THF (50 ml) was added tris-(dimethylamino)-phosphane (10.1 g at 97%, equivalent to 11.2 ml, 60 mmol) in THF (30 ml) within 20 minutes. To the resulting suspension, after stirring for 1 hour at room temperature, was added dropwise a solution of 9-oxo-5-nitro-benzonorbornene (6.10 g, 30 mmol; prepared as described in Example 4) in THF (20 ml) within 25 minutes followed by stirring for 21 hours. The suspension was poured onto ice-water and extracted with ethyl acetate. Purification on silica gel in ethyl acetate-hexane-(1:4) yielded 4.675 g of 9-difluoromethylidene-5-nitro-benzonorbornene (m.p. 99-101° C.).

EXAMPLE 6

This Example illustrates the preparation of 9-Dichloromethylidene-5-nitro-benzonorbornene

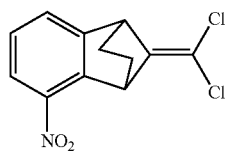 [SMILES: O=[N+]([O-])c1cccc2c1C1CCC2C1=C(Cl)Cl]

Dry carbon tetrachloride (5.9 g, 33 mmol) was reacted with triphenylphosphine (14.46 g, 55.1 mmol) in dichloromethane (30 ml) at room temperature for 1 hour. 9-Oxo-5-nitro-benzonorbornene (5.60 g, 27.56 mmol; prepared as described in Example 4) in dichloromethane (10 ml) was added dropwise and stirred for 20 hours at room temperature. After aqueous work-up (ice-water) and extraction with dichloromethane, the crude product was purified on silica gel in ethyl acetate-hexane-(1:4) to obtain of the desired 9-Dichloromethylidene-5-nitro-benzonorbornene (1.83 g; m.p. 136-137° C.). Some starting material (4.06 g) was recovered.

EXAMPLE 7

This Example illustrates the preparation of 9-Dibromomethylidene-5-nitro-benzonorbornene Carbon tetrabromide (4.66 g at 98%, 13.8 mmol) was reacted under stirring with triphenylphosphine (7.23 g, 27.6 mmol) in dichloromethane (50 ml) for 50 minutes at room temperature. 9-Oxo-5-nitro-benzonorbornene (2.8 g, 13.8 mmol; prepared as described in Example 4) in dichloromethane (10 ml) was added dropwise and stirred over night at room temperature. Aqueous work-up (ice-water) and extraction with dichloromethane followed by column chromatography (ethyl acetate-hexane-(1:9) of the crude product yielded the desired product 9-Dibromomethylidene-5-nitro-benzonorbornene (2.1 g; m.p. 153-155° C.).

TABLE 1

| Compund | m.p (° C.) | $^1$H-NMR proton shifts δ (ppm) (CDCl$_3$) |
|---|---|---|
| A-1.1 | 179-181 | 8.06 (s, 1H), 7.69 (d overlapped by brd signal, exchangeable with D$_2$O, 2H), 7.18 (t, 1H), 7.06 (d, 1H), 4.00 (s, 3H), 3.96 (m, 2H), 2.12 (m, 2H), 1.51 (m, 1H), 1.39 (m, 1H). |
| A-1.2 | 137-143 | 8.06 (s, 1H), 7.68 (brd, exchangeable with D$_2$O, 1H), 7.67 (d, 1H), 7.14 (d, 1H), 4.00 (s, 3H), 3.94 (m, 2H), 2.06 (m, 2H), 1.48 (m, 1H), 1.36 (m.1H). |
| A-1.3 | 198-200 | 8.06 (s, 1H), 7.71 (d, 1H), 7.68 (brd, exchangeable with D$_2$O, 1H), 7.18 (t, 1H), 7.05 (d, 1H), 4.00 (s, 3H), 3.95 (m, 1H), 3.93 (m, 1H), 2.12 (m, 2H), 1.50 (m, 1H), 1.38 (m, 1H). |
| A-1.4 | 183-188 | 7.78 (d, 1H), 7.70 (brd, exchangeable with D$_2$O, 1H), 7.39 (brd s, 1H), 7.16 (t, 1H), 7.01 (d overlapped from brd s, 2H), 4.00 (m, 1H), 3.94 (m, 1H), 3.72 (s, 3H), 2.10 (m, 2H), 1.51 (m, 1H), 1.38 (m, 1H). |
| A-1.5 | 133-135 | 7.76 (d, 1H), 7.70 (brd, exchangeable with D$_2$O, 1H), 7.39 (brd s, 1H), 7.13 (t, 1H), 7.01 (brd s, 1H), 7.00 (d, 1H), 3.98 (m, 1H), 3.93 (m, 1H), 3.72 (s, 3H), 2.04 (m, 2H), 1.49 (m, 1H), 1.36 (m, 1H). |
| A-1.6 | 155-158 | 7.79 (d, 1H), 7.70 (brd, exchangeable with D$_2$O, 1H), 7.39 (brd s, 1H), 7.17 (t, 1H), 7.02 (d, 1H), 7.01 (brd s, 1H), 3.98 (m, 1H), 3.91 (m, 1H), 3.72 (s, 3H), 2.11 (m, 2H), 1.50 (m, 1H), 1.39 (m, 1H). |

Table 1 shows melting point and NMR data, all with CDCl$_3$ as the solvent, unless otherwise stated, for compounds of formula (I).
In the table, temperatures are given in degrees Celsius,
"NMR" means nuclear magnetic resonance spectrum and the following abbreviations are used:
m.p. = melting point
s = singlet
d = doublet
t = triplet
m = multiplet
THF = tetrahydrofuran
b.p. = boiling point.
br = broad
dd = doublet of doublets
q = quartet
ppm = parts per million The components (B) are known. Where the components (B) are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular component (B); for example, the compound "abamectin" is described under entry number (1). Most of the components (B) are referred to hereinabove by a so-called "common name", the relevant "ISO common name" or another "common name" being used in individual cases. If the designation is not a "common name", the nature of the designation used instead is given in round brackets for the particular component (B); in that case, the IUPAC name, the IUPAC/Chemical Abstracts name, a "chemical name", a "traditional name", a "compound name" or a "development code" is used or, if neither one of those designations nor a "common name" is used, an "alternative name" is employed.

The following components B) are registered under a CAS-Reg. No.
aldimorph (CAS 91315-15-0); arsenates (CAS 1327-53-3); benalaxyl-M (CAS 98243-83-5); benthiavalicarb (CAS 413615-35-7); cadmium chloride (CAS 10108-64-2); cedar leaf oil (CAS 8007-20-3); chlorine (CAS 7782-50-5); cinnamaldehyde (CAS: 104-55-2); copper ammoniumcarbonate (CAS 33113-08-5); copper oleate (CAS 1120-44-1); iodocarb (3-Iodo-2-propynyl butyl carbamate) (CAS 55406-53-6); hymexazole (CAS 10004-44-1); manganous dimethyldithiocarbamate (CAS 15339-36-3); mercury (CAS 7487-94-7; 21908-53-2; 7546-30-7); metrafenone (CAS 220899-03-6); neem oil (hydrophobic extract) (CAS 8002-65-1); orysastrobin CAS 248593-16-0); paraformaldehyde (CAS 30525-89-4); penthiopyrad (CAS 183675-82-3); phosphoric acid (CAS 7664-38-2); potassium bicarbonate (CAS 298-14-6); sodium bicarbonate (CAS 144-55-8); sodium diacetate (CAS 127-09-3); sodium propionate (CAS 137-40-6); TCMTB (CAS 21564-17-0); and tolyfluanid (CAS 731-27-1).

Compound B-1.1 ("enestrobin") is described in EP-0-936-213; compound B-3.1 ("flumorph") in U.S. Pat. No. 6,020,332, CN-1-167-568, CN-1-155-977 and in EP-0-860-438; compound B-5.1 ("mandipropamid") in WO 01/87822; compound B-5.2 in WO 98/46607; compound B-5.3 ("fluopicolide") in WO 99/42447; compound B-5.4 ("cyflufenamid") in WO 96/19442; compound B-5.5 in WO 99/14187; compound B-5.6 ("pyribencarb") is registered under CAS-Reg. No. 325156-49-8; compound B-5.7 ("amisulbrom" or "ambromdole") is registered under CAS. Reg. No. 348635-87-0; compound B-5.8 (3-difluoromethyl-1-methyl-1H-pyrazole-4-carboxylic acid (2-bicyclopropyl-2-yl-phenyl)-amide) is described in WO 03/74491; compound B-5.9 (3-difluoromethyl-1-methyl-1H-pyrazole-4-carboxylic acid (9-isopropyp-1,2,3,4-tetrahydro-1,4-methano-naphthalen-5-yl)-amide) is described in WO 04/35589 and in WO 06/37632; compound B-5.10 (1,3-dimethyl-5-fluoro-1H-pyrazole-4-carboxylic acid [2-(1,3-dimethylbutyl)phenyl]-amide) is described in WO 03/10149; compound B-5.11 (3-difluoromethyl-1-methyl-1H-pyrazole-4-carboxylic acid (3',4'-dichloro-5-fluoro-1,1'-biphenyl-2-yl)-amide; "bixafen") is registered under CAS-Reg. No.: 581809-46-3 and described in WO 03/70705; compound B-5.12 (N-{2-[3-Chloro-5-(trifluoromethyl)pyridin-2-yl]ethyl}-2-(trifluoromethyl)benzamid; "fluopyram") is registered under CAS-Reg. No: 658066-35-4 and described in WO 04/16088; compounds B-5.13, B-5.14 and B-5.15 are described in WO 07/17450; compounds B-5.16, B-5.17 and B-5.18 are described in WO 06/120219; The compounds of formula IV are for example described in WO 04/067528, WO 2005/085234, WO 2006/111341, WO 03/015519, WO 2007/020050, WO 2006/040113, and WO 2007/093402. The compound of formula V is described in WO 01/94339. The compounds of formula VIa, VIb and VIc is described in WO 04/35589 and in PCT/EP2005/010755. Fomesafen is registered under the CAS-Reg. No. 72178-02-0.

Examples of especially suitable compounds as component (B) are compounds selected from the following group P:

Group P: Especially Suitable Compounds as Component (B) in the Compositions According to the Invention:

a strobilurin fungicide selected from azoxystrobin (47), dimoxystrobin (226), fluoxastrobin (382), kresoxim-methyl (485), metominostrobin (551), orysastrobin, picoxystrobin (647), pyraclostrobin (690); trifloxystrobin (832), a compound of formula B-1.1

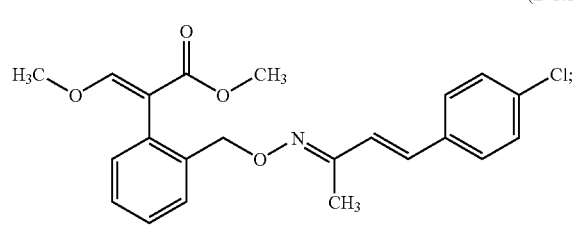

(B-1.1)

an azole fungicide selected from azaconazole (40), bromuconazole (96), cyproconazole (207), difenoconazole (247), diniconazole (267), diniconazole-M (267), epoxiconazole (298), fenbuconazole (329), fluquinconazole (385), flusilazole (393), flutriafol (397), hexaconazole (435), imazalil (449), imibenconazole (457), ipconazole (468), metconazole (525), myclobutanil (564), oxpoconazole (607), pefurazoate (618), penconazole (619), prochloraz (659), propiconazole (675), prothioconazole (685), simeconazole (731), tebuconazole (761), tetraconazole (778), triadimefon (814), triadimenol (815), triflumizole (834), triticonazole (842), diclobutrazol (1068), etaconazole (1129), furconazole (1198), furconazole-cis (1199) and quinconazole (1378);

a morpholine fungicide selected from aldimorph, dodemorph (288), fenpropimorph (344), tridemorph (830), fenpropidin (343), spiroxamine (740), piperalin (648) and a compound of formula B-3.1

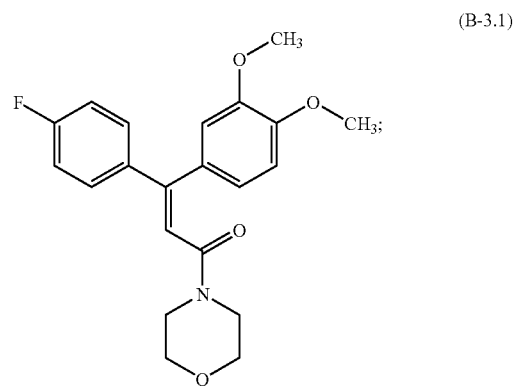 [SMILES: COc1ccc(/C(=C\C(=O)N2CCOCC2)c2ccc(F)cc2)cc1OC]

(B-3.1)

an anilino-pyrimidine fungicide selected from cyprodinil (208), mepanipyrim (508) and pyrimethanil (705);

a fungicide selected from the group consisting of anilazine (878), arsenates, benalaxyl (56), benalaxyl-M, benodanil (896), benomyl (62), benthiavalicarb, benthiavalicarb-isopropyl (68), biphenyl (81), bitertanol (84), blasticidin-S (85), bordeaux mixture (87), boscalid (88), bupirimate (98), cadmium chloride, captafol (113), captan (114), carbendazim (116), carbon disulfide (945), carboxin (120), carpropamid (122), cedar leaf oil, chinomethionat (126), chlorine, chloroneb (139), chlorothalonil (142), chlozolinate (149), cinnamaldehyde, copper, copper ammoniumcarbonate, copper hydroxide (169), copper octanoate (170), copper oleate, copper sulphate (87), cyazofamid (185), cycloheximide (1022), cymoxanil (200), dichlofluanid (230), dichlone (1052), dichloropropene (233), diclocymet (237), diclomezine (239), dicloran (240), diethofencarb (245), diflumetorim (253), dimethirimol (1082), dimethomorph (263), dinocap (270), dithianon (279), dodine (289), edifenphos (290), ethaboxam (304), ethirimol (1133), etridiazole (321), famoxadone (322), fenamidone (325), fenaminosulf (1144), fenamiphos (326), fenarimol (327), fenfuram (333), fenhexamid (334), fenoxanil (338), fenpiclonil (341), fentin acetate (347), fentin chloride, fentin hydroxide (347), ferbam (350), ferimzone (351), fluazinam (363), fludioxonil (368), flusulfamide (394), flutolanil (396), folpet (400), formaldehyde (404), fosetyl-aluminium (407), fthalide (643), fuberidazole (419), furalaxyl (410), furametpyr (411), flyodin (1205), fuazatine (422), hexachlorobenzene (434), hymexazole, iminoctadine (459), iodocarb (3-Iodo-2-propynyl butyl carbamate), iprobenfos (IBP) (469), iprodione (470), iprovalicarb (471), isoprothiolane (474), kasugamycin (483), mancozeb (496), maneb (497), manganous dimethyldithiocarbamate, mefenoxam (Metalaxyl-M) (517), mepronil (510), mercuric chloride (511), mercury, metalaxyl (516), methasulfocarb (528), metiram (546), metrafenone, nabam (566), neem oil (hydrophobic extract), nuarimol (587), octhilinone (590), ofurace (592), oxadixyl (601), oxine copper (605), oxolinic acid (606), oxycarboxin (608), oxytetracycline (611), paclobutrazole (612), paraffin oil (628), paraformaldehyde, pencycuron (620), pentachloronitrobenzene (716), pen tachlorophenol (623), penthiopyrad, perfurazoate, phosphoric acid, polyoxin (654), polyoxin D zinc salt (654), potassium bicarbonate, probenazole (658), procymidone (660), propamocarb (668), propineb (676), proquinazid (682), prothiocarb (1361), pyrazophos (693), pyrifenox (703), pyroquilon (710), quinoxyfen (715), quintozene (PCNB) (716), silthiofam (729), sodium bicarbonate, sodium diacetate, sodium propionate, streptomycin (744), sulphur (754), TCMTB, tecloftalam, tecnazene (TCNB) (767), thiabendazole (790), thifluzamide (796), thiophanate (1435), thiophanate-methyl (802), thiram (804), tolclofos-methyl (808), tolylfluanid (810), triazoxide (821), trichoderma harzianum (825), tricyclazole (828), triforine (838), triphenyltin hydroxide (347), validamycin (846), vinclozolin (849), zineb (855), ziram (856), zoxamide (857), 1,1-bis(4-chlorophenyl)-2-ethoxyethanol (IUPAC-Name) (910), 2,4-dichlorophenyl benzenesulfonate (IUPAC-/Chemical Abstracts-Name) (1059), 2-fluoro-N-methyl-N-1-naphthylacetamide (IUPAC-Name) (1295), 4-chlorophenyl phenyl sulfone (IUPAC-Name) (981), a compound of formula B-5.1, a compound of formula B-5.2, a compound of formula B-5.3, a compound of formula B-5.4, a compound of formula B-5.5, a compound of formula B-5.6, a compound of formula B-5.7, compound B-5.8, compound B-5.9, compound B-5.10, compound B-5.11, compound B-5.12, compound B-5.13, compound B-5.14, compound B-5.15, compound B-5.16, compound B-5.17 and compound B-5.18;

a plant-bioregulator selected from the group consisting of acibenzolar-S-methyl (6), chlormequat chloride (137), ethephon (307), mepiquat chloride (509) and trinexapc-ethyl (841);

an insecticide selected from the group consisting of abamectin (1), clothianidin (165), emamectin benzoate (291), imidacloprid (458), tefluthrin (769), thiamethoxam (792), and glyphosate (419), a compound of formula V

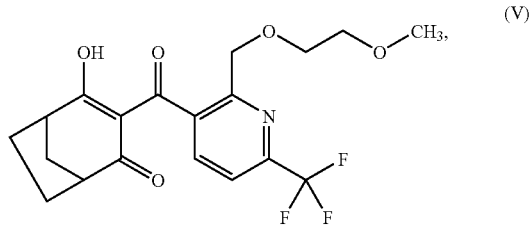

fomesafen, and (B9) a racemic compound of formula VIa (syn)

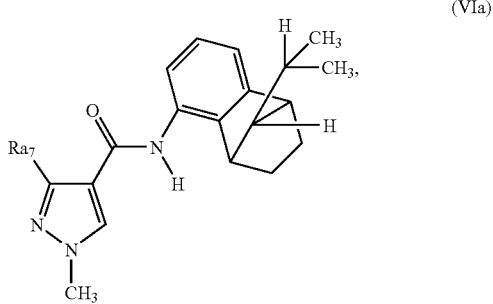

wherein Ra$_7$ is trifluoromethyl or difluoromethyl; a racemic mixture of formula VIb (anti)

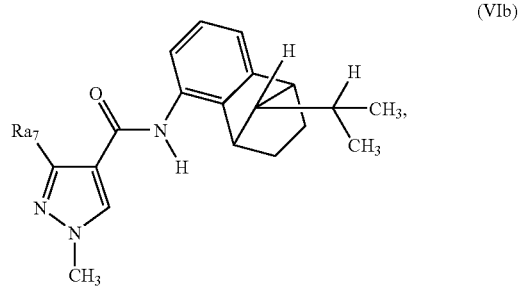

wherein Ra$_7$ is trifluoromethyl or difluoromethyl; a compound of formula VIc

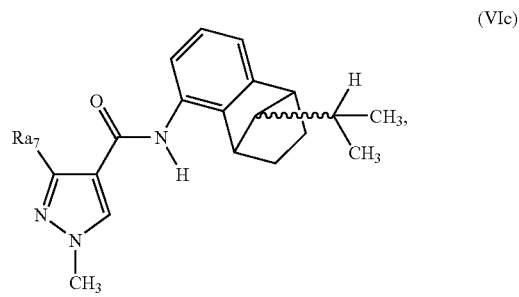

which is an epimeric mixture of racemic compounds of formulae F-10 (syn) and F-11 (anti), wherein the ratio from racemic compounds of formula F-10 (syn) to racemic compounds of formula F-11 (anti) is from 1000:1 to 1:1000 and wherein Ra$_7$ is trifluoromethyl or difluoromethyl.

Further examples of especially suitable compounds as component (B) are compounds selected from the following group Q:

Group Q: Especially Suitable Compounds as Component (B) in the Compositions According to the Invention:

a strobilurin fungicide selected from the group consisting of azoxystrobin, dimoxystrobin, fluoxastrobin, kresoxim-methyl, metominostrobin, orysastrobin, picoxystrobin, pyraclostrobin; trifloxystrobin and a compound of formula B-1.1;

an azole fungicide selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imazalil, imibenconazole, ipconazole, metconazole, myclobutanil, oxpoconazole, pefurazoate, penconazole, prochloraz, propiconazole, prothioconazole, simeconazole, tebuconazole, tetraconazole, triadimefon, triadimenol, triflumizole, triticonazole, diclobutrazol, etaconazole, furconazole, furconazole-cis and quinconazole;

a morpholine fungicide selected from the group consisting of aldimorph, dodemorph, fenpropimorph, tridemorph, fenpropidin, spiroxamine, piperalin and a compound of formula B-3.1;

an anilino-pyrimidine fungicide selected from the group consisting of cyprodinil, mepanipyrim and pyrimethanil;

a fungicide selected from the group consisting of benalaxyl, benalaxyl-M, benomyl, bitertanol, boscalid, captan, carboxin, carpropamid, chlorothalonil, copper, cyazofamid, cymoxanil, diethofencarb, dithianon, famoxadone, fenamidone, fenhexamide, fenoxycarb, fenpiclonil, fluazinam, fludioxonil, flutolanil, folpet, guazatine, hymexazole, iprodione, lufenuron, mancozeb, metalaxyl, mefenoxam, metrafenone, nuarimol, paclobutrazol, pencycuron, penthiopyrad, procymidone, proquinazid, pyroquilon, quinoxyfen, silthiofam, sulfur, thiabendazole, thiram, triazoxide, tricyclazole, a compound of formula B-5.1, a compound of formula B-5.2, a compound of formula B-5.3, a compound of formula B-5.4, a compound of formula B-5.5, a compound of formula B-5.6, a compound of formula B-5.7, a compound of formula B-5.8, a compound of formula B-5.9, a compound of formula B-5.10 and a compound of formula B-5.12;

a plant-bioregulator selected from acibenzolar-5-methyl, chlormequat chloride, ethephon, mepiquat chloride and trinexapc-ethyl;

an insecticide selected from abamectin, emamectin benzoate, tefluthrin, thiamethoxam, and glyphosate, a compound of formula V

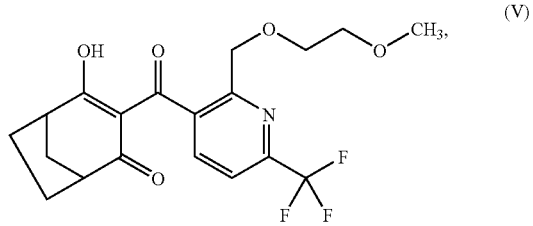

fomesafen, and (B9) a racemic compound of formula VIa (syn)

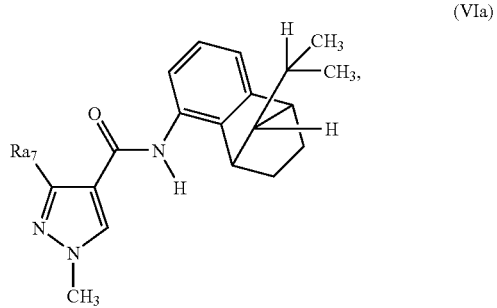

wherein Ra$_7$ is trifluoromethyl or difluoromethyl; a racemic mixture of formula VIb (anti)

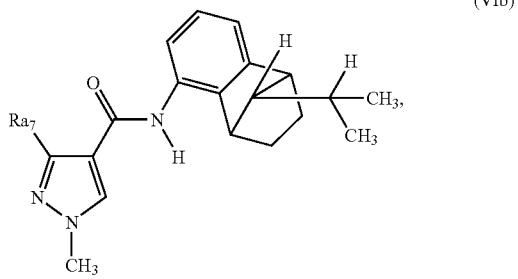

wherein Ra$_7$ is trifluoromethyl or difluoromethyl; a compound of formula VIc

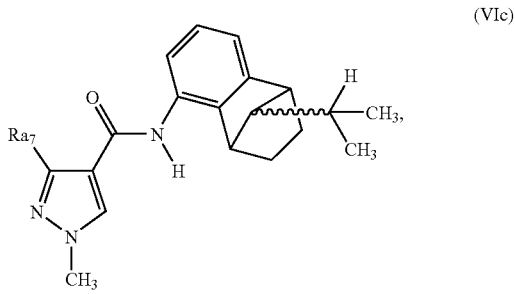

which is an epimeric mixture of racemic compounds of formulae F-10 (syn) and F-11 (anti), wherein the ratio from racemic compounds of formula F-10 (syn) to racemic compounds of formula F-11 (anti) is from 1000:1 to 1:1000 and wherein Ra$_7$ is trifluoromethyl or difluoromethyl.

Throughout this document the expression "composition" stands for the various mixtures or combinations of components (A) and (B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components (A) and (B) is not essential for working the present invention.

The compositions according to the invention may also comprise more than one of the active components (B), if, for example, a broadening of the spectrum of phytopathogenic disease control is desired. For instance, it may be advantageous in the agricultural practice to combine two or three components (B) with component (A). An example is a composition comprising a compound of formula (I), azoxystrobin and cyproconazole.

Further examples for compositions according to the present invention which comprise three active ingredients are defined as embodiments E1 and E2:

Embodiment E1

The term "TX1" means: "the compound A-1.1+ a compound selected from the group P"

Dimoxystrobin+TX1, fluoxastrobin+TX1, kresoxim-methyl+TX1, metominostrobin+TX1, orysastrobin+TX1, picoxystrobin+TX1, pyraclostrobin+TX1, trifloxystrobin+TX1, a compound of formula B-1.1+TX1, azaconazole+TX1, bromuconazole+TX1, cyproconazole+TX1, difenoconazole+TX1, diniconazole+TX1, diniconazole-M+TX1, epoxiconazole+TX1, fenbuconazole+TX1, fluquinconazole+TX1, flusilazole+TX1, flutriafol+TX1, hexaconazole+TX1, imazalil+TX1, imibenconazole+TX1, ipconazole+TX1, metconazole+TX1, myclobutanil+TX1, oxpoconazole+TX1, pefurazoate+TX1, penconazole+TX1, prochloraz+TX1, propiconazole+TX1, prothioconazole+TX1, simeconazole+TX1, tebuconazole+TX1, tetraconazole+TX1, triadimefon+TX1, triadimenol+TX1, triflumizole+TX1, triticonazole+TX1, diclobutrazol+TX1, etaconazole+TX1, furconazole+TX1, furconazole-cis+TX1, quinconazole+TX1, aldimorph+TX1, dodemorph+TX1, fenpropimorph+TX1, tridemorph+TX1, fenpropidin+TX1, spiroxamine+TX1, piperalin+TX1, a compound of formula B-3.1+TX1, cyprodinil+TX1, mepanipyrim+TX1, pyrimethanil+TX1, benalaxyl+TX1, benalaxyl-M+TX1, benomyl+TX1, bitertanol+TX1, boscalid+TX1, captan+TX1, carboxin+TX1, carpropamid+TX1, chlorothalonil+TX1, copper+TX1, cyazofamid+TX1, cymoxanil+TX1, diethofencarb+TX1, dithianon+TX1, famoxadone+TX1, fenamidone+TX1, fenhexamide+TX1, fenoxycarb+TX1, fenpiclonil+TX1, fluazinam+TX1, fludioxonil+TX1, flutolanil+TX1, folpet+TX1, guazatine+TX1, hymexazole+TX1, iprodione+TX1, lufenuron+TX1, mancozeb+TX1, metalaxyl+TX1, mefenoxam+TX1, metrafenone+TX1, nuarimol+TX1, paclobutrazol+TX1, pencycuron+TX1, penthiopyrad+TX1, procymidone+TX1, proquinazid+TX1, pyroquilon+TX1, quinoxyfen+TX1, silthiofam+TX1, sulfur+TX1, thiabendazole+TX1, thiram+TX1, triazoxide+TX1, tricyclazole+TX1, a compound of formula B-5.1+TX1, a compound of formula B-5.2+TX1, a compound of formula B-5.3+TX1, a compound of formula B-5.4+TX1, a compound of formula B-5.5+TX1, a compound of formula B-5.6+TX1, a compound of formula B-5.7+TX1, a compound of formula B-5.8+TX1, a compound of formula B-5.9+TX1, a compound of formula B-5.10+TX1, a compound of formula B-5.12+TX1, acibenzolar-5-methyl+TX1, chlormequat chloride+TX1, ethephon+TX1, mepiquat chloride+TX1, trinexapc-ethyl+TX1, abamectin+TX1, emamectin benzoate+TX1, tefluthrin+TX1, thiamethoxam+TX1 and glyphosate+TX1.

Embodiment E2

The term "TX2" means: "the compound A-1.2+ a compound selected from the group P".

Dimoxystrobin+TX2, fluoxastrobin+TX2, kresoxim-methyl+TX2, metominostrobin+TX2, orysastrobin+TX2, picoxystrobin+TX2, pyraclostrobin+TX2, trifloxystrobin+TX2, a compound of formula B-1.1+TX2, azaconazole+TX2, bromuconazole+TX2, cyproconazole+TX2, difenoconazole+TX2, diniconazole+TX2, diniconazole-M+TX2, epoxiconazole+TX2, fenbuconazole+TX2, fluquinconazole+TX2, flusilazole+TX2, flutriafol+TX2, hexaconazole+TX2, imazalil+TX2, imibenconazole+TX2, ipconazole+TX2, metconazole+TX2, myclobutanil+TX2, oxpoconazole+TX2, pefurazoate+TX2, penconazole+TX2, prochloraz+TX2, propiconazole+TX2, prothioconazole+TX2, simeconazole+TX2, tebuconazole+TX2, tetraconazole+TX2, triadimefon+TX2, triadimenol+TX2, triflumizole+TX2, triticonazole+TX2, diclobutrazol+TX2, etaconazole+TX2, furconazole+TX2, furconazole-cis+TX2, quinconazole+TX2, aldimorph+TX2, dodemorph+TX2, fenpropimorph+TX2, tridemorph+TX2, fenpropidin+TX2, spiroxamine+TX2, piperalin+TX2, a compound of formula B-3.1+TX2, cyprodinil+TX2, mepanipyrim+TX2, pyrimethanil+TX2, benalaxyl+TX2, benalaxyl-M+TX2, benomyl+TX2, bitertanol+TX2, boscalid+TX2, captan+TX2, carboxin+TX2, carpropamid+TX2, chlorothalonil+TX2, copper+TX2, cyazofamid+TX2, cymoxanil+TX2, diethofencarb+TX2, dithianon+TX2, famoxadone+TX2, fenamidone+TX2, fenhexamide+TX2, fenoxycarb+TX2, fenpiclonil+TX2, fluazinam+TX2, fludioxonil+TX2, flutolanil+TX2, folpet+TX2, guazatine+TX2, hymexazole+TX2, iprodione+TX2, lufenuron+TX2, mancozeb+TX2, metalaxyl+TX2, mefenoxam+TX2, metrafenone+TX2, nuarimol+TX2, paclobutrazol+TX2, pencycuron+TX2, penthiopyrad+TX2, procymidone+TX2, proquinazid+TX2, pyroquilon+TX2, quinoxyfen+TX2, silthiofam+TX2, sulfur+TX2, thiabendazole+TX2, thiram+TX2, triazoxide+TX2, tricyclazole+TX2, a compound of formula B-5.1+TX2, a compound of formula B-5.2+TX2, a compound of formula B-5.3+TX2, a compound of formula B-5.4+TX2, a compound of formula B-5.5+TX2, a compound of formula B-5.6+TX2, a compound of formula B-5.7+TX2, a compound of formula B-5.8+TX2, a compound of formula B-5.9+TX2, a compound of formula B-5.10+TX2, a compound of formula B-5.12+TX2, acibenzolar-5-methyl+TX2, chlormequat chloride+TX2, ethephon+TX2, mepiquat chloride+TX2, trinexapc-ethyl+TX2, abamectin+TX2, emamectin benzoate+TX2, tefluthrin+TX2, thiamethoxam+TX2 and glyphosate+TX2.

The embodiments E1 and E2 define compositions according to the present invention which comprise 3 active ingredients. In said embodiments, the mixing partner selected from the group P has to be different from the other described mixing partners. For example, the composition "cyproconazole+TX1" means compositions comprising as active ingredients cyproconazole, the compound A-1.1+ a compound selected from the group P. In said compositions, the compound selected from the group P is different from cyproconazole.

The following compositions are preferred:

A composition comprising (A) compound A-1.1 and (B) a compound selected from the group P. An example of such a composition is a composition comprising the compound A-1.1 and the first compound from the group P, which is azoxystrobin.

A composition comprising (A) compound A-1.1 and (B) a compound selected from the group Q. An example of such a composition is a composition comprising the compound A-1.1 and the second compound from the group Q, which is dimoxystrobin.

A composition comprising (A) compound A-1.1 and (B) a strobilurin fungicide.

A composition comprising (A) compound A-1.1 and (B) an azole fungicide.

A composition comprising (A) compound A-1.1 and (B) a morpholine fungicide.

A composition comprising (A) compound A-1.1 and (B) an anilinopyrimidine fungicide.

A composition comprising (A) compound A-1.1 and the insecticide of formula B-7.1.

A composition comprising (A) compound A-1.1 and (B) a glyphosate.

A composition comprising (A) compound A-1.1 and a fungicide selected from azoxystrobin, fluoxastrobin, picoxystrobin, pyraclostrobin, trifloxystrobin, cyproconazole, difenoconazole, epoxiconazole, flutriafol, ipconazole, metconazole, myclobutanil, penconazole, propiconazole, prothioconazole, tebuconazole, tetraconazole, fenpropidin, cyprodinil, chlorothalonil, dithianon, fluazinam, fludioxonil, metrafenone, compound B-5.1 and compound B-5.4.

A composition comprising (A) compound A-1.1 and a fungicide selected from azoxystrobin, fluoxastrobin, picoxystrobin, pyraclostrobin, trifloxystrobin, cyproconazole, epoxiconazole, flutriafol, ipconazole, metconazole, myclobutanil, propiconazole, prothioconazole, tebuconazole, tetraconazole and chlorothalonil.

A composition comprising (A) compound A-1.2 and (B) a compound selected from the group P.

A composition comprising (A) compound A-1.2 and (B) a compound selected from the group Q.

A composition comprising (A) compound A-1.2 and (B) a strobilurin fungicide.

A composition comprising (A) compound A-1.2 and (B) an azole fungicide.

A composition comprising (A) compound A-1.2 and (B) a morpholine fungicide.

A composition comprising (A) compound A-1.2 and (B) an anilinopyrimidine fungicide.

A composition comprising (A) compound A-1.2 and the insecticide of formula B-7.1.

A composition comprising (A) compound A-1.2 and (B) a glyphosate.

A composition comprising (A) compound A-1.2 and a fungicide selected from azoxystrobin, fluoxastrobin, picoxystrobin, pyraclostrobin, trifloxystrobin, cyproconazole, difenoconazole, epoxiconazole, flutriafol, ipconazole, metconazole, myclobutanil, penconazole, propiconazole, prothioconazole, tebuconazole, tetraconazole, fenpropidin, cyprodinil, chlorothalonil, dithianon, fluazinam, fludioxonil, metrafenone, compound B-5.1 and compound B-5.4.

A composition comprising (A) compound A-1.2 and a fungicide selected from azoxystrobin, fluoxastrobin, picoxystrobin, pyraclostrobin, trifloxystrobin, cyproconazole, epoxiconazole, flutriafol, ipconazole, metconazole, myclobutanil, propiconazole, prothioconazole, tebuconazole, tetraconazole and chlorothalonil.

A composition comprising (A) compound A-1.3 and (B) a compound selected from the group P.

A composition comprising (A) compound A-1.3 and (B) a compound selected from the group Q.

A composition comprising (A) compound A-1.3 and (B) a strobilurin fungicide.

A composition comprising (A) compound A-1.3 and (B) an azole fungicide.

A composition comprising (A) compound A-1.3 and (B) a morpholine fungicide.

A composition comprising (A) compound A-1.3 and (B) an anilinopyrimidine fungicide.

A composition comprising (A) compound A-1.3 and the insecticide of formula B-7.1.

A composition comprising (A) compound A-1.3 and (B) a glyphosate.

A composition comprising (A) compound A-1.3 and a fungicide selected from azoxystrobin, fluoxastrobin, picoxystrobin, pyraclostrobin, trifloxystrobin, cyproconazole, difenoconazole, epoxiconazole, flutriafol, ipconazole, metconazole, myclobutanil, penconazole, propiconazole, prothioconazole, tebuconazole, tetraconazole, fenpropidin, cyprodinil, chlorothalonil, dithianon, fluazinam, fludioxonil, metrafenone, compound B-5.1 and compound B-5.4.

A composition comprising (A) compound A-1.3 and a fungicide selected from azoxystrobin, fluoxastrobin, picoxystrobin, pyraclostrobin, trifloxystrobin, cyproconazole, epoxiconazole, flutriafol, ipconazole, metconazole, myclobutanil, propiconazole, prothioconazole, tebuconazole, tetraconazole and chlorothalonil.

A composition comprising (A) compound A-1.4 and (B) a compound selected from the group P.

A composition comprising (A) compound A-1.5 and (B) a compound selected from the group P.

A composition comprising (A) compound A-1.6 and (B) a compound selected from the group P.

The compositions according to the invention are effective against harmful microorganisms, such as microorganisms, that cause phytopathogenic diseases, in particular against phytopathogenic fungi and bacteria.

The compositions according to the invention are effective especially against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago, Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*).

According to the invention "useful plants" typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants.

Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compositions of the present invention may also be used in the field of protecting storage goods against attack of fungi. According to the present invention, the term "storage goods" is understood to denote natural substances of vegetable and/or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The compositions according the present invention can prevent disadvantageous effects such as decay, discoloration or mold. Preferably "storage goods" is understood to denote natural substances of vegetable origin and/or their processed forms, more preferably fruits and their processed forms, such as pomes, stone fruits, soft fruits and citrus fruits and their processed forms. In another preferred embodiment of the invention "storage goods" is understood to denote wood.

Therefore a further aspect of the present invention is a method of protecting storage goods, which comprises applying to the storage goods a composition according to the invention.

The compositions of the present invention may also be used in the field of protecting technical material against attack of fungi. According to the present invention, the term "technical material" includes paper; carpets; constructions; cooling and heating systems; wall-boards; ventilation and air conditioning systems and the like; preferably "technical material" is understood to denote wall-boards. The compositions according the present invention can prevent disadvantageous effects such as decay, discoloration or mold.

The compositions according to the invention are particularly effective against powdery mildews; rusts; leafspot species; early blights and molds; especially against *Septoria, Puccinia, Erysiphe, Pyrenophora* and *Tapesia* in cereals; *Phakopsora* in soybeans; *Hemileia* in coffee; *Phragmidium* in roses; *Alternaria* in potatoes, tomatoes and cucurbits; *Sclerotinia* in turf, vegetables, sunflower and oil seed rape; black rot, red fire, powdery mildew, grey mold and dead arm disease in vine; *Botrytis cinerea* in fruits; *Monilinia* spp. in fruits and *Penicillium* spp. in fruits.

The compositions according to the invention are furthermore particularly effective against seedborne and soilborne diseases, such as *Alternaria* spp., *Ascochyta* spp., *Botrytis cinerea, Cercospora* spp., *Claviceps purpurea, Cochliobolus sativus, Colletotrichum* spp., *Epicoccum* spp., *Fusarium graminearum, Fusarium moniliforme, Fusarium oxysporum, Fusarium proliferatum, Fusarium solani, Fusarium subglutinans, Gäumannomyces graminis, Helminthosporium* spp., *Microdochium nivale, Phoma* spp., *Pyrenophora graminea, Pyricularia oryzae, Rhizoctonia solani, Rhizoctonia cerealis, Sclerotinia* spp., *Septoria* spp., *Sphacelotheca reilliana, Tilletia* spp., *Typhula incarnata, Urocystis occulta, Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

The compositions according to the invention are furthermore particularly effective against post harvest diseases such as *Botrytis cinerea, Colletotrichum musae, Curvularia lunata, Fusarium semitecum, Geotrichum candidum, Monilinia fructicola, Monilinia fructigena, Monilinia laxa, Mucor piriformis, Penicilium italicum, Penicilium solitum, Penicillium digitatum* or *Penicillium expansum* in particular against pathogens of fruits, such as pomefruits, for example apples and pears, stone fruits, for example peaches and plums, citrus, melons, papaya, kiwi, mango, berries, for example strawberries, avocados, pomegranates and bananas, and nuts.

The compositions according to the invention are particularly useful for controlling the following diseases on the following crops:
*Alternaria* species in fruit and vegetables; *Ascochyta* species in pulse crops; *Botrytis cinerea* in strawberries, tomatoes, sunflower, pulse crops, vegetables and grapes, such as *Botrytis cinerea* on grape; *Cercospora arachidicola* in peanuts; *Cochliobolus sativus* in cereals; *Colletotrichum* species in pulse crops; *Erysiphe* species in cereals; such as *Erysiphe graminis* on wheat and *Erysiphe graminis* on barley; *Erysiphe cichoracearum* and *Sphaerotheca fuliginea* in cucurbits; *Fusarium* species in cereals and maize; *Gäumannomyces graminis* in cereals and lawns; *Helminthosporium* species in maize, rice and potatoes; *Hemileia vastatrix* on coffee; *Microdochium* species in wheat and rye; *Mycosphaerella fijiensis* in banana; *Phakopsora* species in soybeans, such as *Phakopsora pachyrizi* in soybeans; *Puccinia* species in cereals, broadleaf crops and perennial plants; such as *Puccinia recondita* on wheat, *Puccinia striiformis* on wheat and *Puccinia recondita* on barley; *Pseudocercosporella* species in cereals, such as *Pseudocercosporella herpotrichoides* in wheat; *Phragmidium mucronatum* in roses; *Podosphaera* species in fruits; *Pyrenophora* species in barley, such as *Pyrenophora teres* on barley; *Pyricularia oryzae* in rice; *Ramularia collo-cygni* in barley; *Rhizoctonia* species in cotton, soybean, cereals, maize, potatoes, rice and lawns, such as *Rhizoctonia solani* on potato, rice, turf and cotton; *Rhynchosporium secalis* on barley, *Rhynchosporium secalis* on rye; *Sclerotinia* species in lawns, lettuce, vegetables and oil seed rape, such as *Sclerotinia sclerotiorum* on oilseed rape and *Sclerotinia homeocarpa* on turf; *Septoria* species in cereals, soybean and vegetables, such as *Septoria tritici* on wheat, *Septoria nodorum* on wheat and *Septoria* glycines on soybean; *Sphacelotheca reilliana* in maize; *Tilletia* species in cereals; *Uncinula necator, Guignardia bidwellii* and *Phomopsis viticola* in vines; *Urocystis occulta* in rye; *Uromyces* species in beans; *Ustilago* species in cereals and maize; *Venturia* species in fruits, such as *Venturia inequalis* on apple; *Monilinia* species on fruits; *Penicillium* species on citrus and apples.

In general, the weight ratio of component (A) to component (B) is from 2000:1 to 1:1000. A non-limiting example for such weight ratios is compound of formula I:compound of formula B-2 is 10:1. The weight ratio of component (A) to component (B) is preferably from 100:1 to 1:100; more preferably from 20:1 to 1:50.

It has been found, surprisingly, that certain weight ratios of component (A) to component (B) are able to give rise to synergistic activity. Therefore, a further aspect of the invention are compositions, wherein component (A) and component (B) are present in the composition in amounts producing a synergistic effect. This synergistic activity is apparent from the fact that the fungicidal activity of the composition comprising component (A) and component (B) is greater than the sum of the fungicidal activities of component (A) and of component (B). This synergistic activity extends the range of action of component (A) and component (B) in two ways. Firstly, the rates of application of component (A) and component (B) are lowered whilst the action remains equally good, meaning that the active ingredient mixture still achieves a high degree of phytopathogen control even where the two individual components have become totally ineffective in such a low application rate range. Secondly, there is a substantial broadening of the spectrum of phytopathogens that can be controlled.

A synergistic effect exists whenever the action of an active ingredient combination is greater than the sum of the actions of the individual components. The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967): ppm=milligrams of active ingredient (=a.i.) per liter of spray mixture
X=% action by active ingredient A) using p ppm of active ingredient
Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms, synergism corresponds to a positive value for the difference of (O−E). In the case of purely complementary addition of activities (expected activity), said difference (O−E) is zero. A negative value of said difference (O−E) signals a loss of activity compared to the expected activity.

However, besides the actual synergistic action with respect to fungicidal activity, the compositions according to the invention can also have further surprising advantageous properties. Examples of such advantageous properties that may be mentioned are: more advantageous degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

Some compositions according to the invention have a systemic action and can be used as foliar, soil and seed treatment fungicides.

With the compositions according to the invention it is possible to inhibit or destroy the phytopathogenic microorganisms which occur in plants or in parts of plants (fruit, blossoms, leaves, stems, tubers, roots) in different useful plants, while at the same time the parts of plants which grow later are also protected from attack by phytopathogenic microorganisms.

The compositions according to the invention can be applied to the phytopathogenic microorganisms, the useful plants, the locus thereof, the propagation material thereof, storage goods or technical materials threatened by microorganism attack.

The compositions according to the invention may be applied before or after infection of the useful plants, the propagation material thereof, storage goods or technical materials by the microorganisms.

The amount of a composition according to the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

When applied to the useful plants component (A) is typically applied at a rate of 5 to 2000 g a.i./ha, particularly 10 to 1000 g a.i./ha, e.g. 50, 75, 100 or 200 g a.i./ha, typically in association with 1 to 5000 g a.i./ha, particularly 2 to 2000 g a.i./ha, e.g. 100, 250, 500, 800, 1000, 1500 g a.i./ha of component (B).

In agricultural practice the application rates of the compositions according to the invention depend on the type of effect desired, and typically range from 20 to 4000 g of total composition per hectare.

When the compositions according to the invention are used for treating seed, rates of 0.001 to 50 g of a compound of component (A) per kg of seed, preferably from 0.01 to 10 g per kg of seed, and 0.001 to 50 g of a compound of component (B), per kg of seed, preferably from 0.01 to 10 g per kg of seed, are generally sufficient.

The composition of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with at least one appropriate inert formulation adjuvant (for example, diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

The compositions according to the invention may also comprise further pesticides, such as, for example, fungicides, insecticides or herbicides.

A seed dressing formulation is applied in a manner known per se to the seeds employing the compositions according to the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least a compound of component (A) together with a compound of component (B), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Surprisingly it has been found that compounds of formula (I)

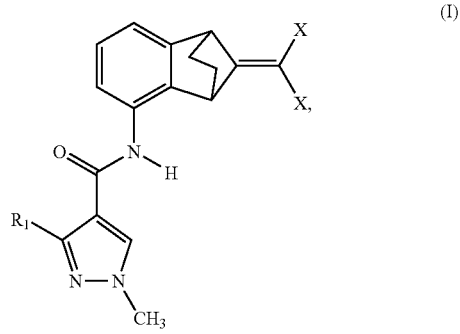

(I)

wherein $R_1$ is difluoromethyl or trifluoromethyl and X is chloro, fluoro or bromo; have good activity against soybean rust diseases, such as diseases caused by *Phakopsora pachyrhizi* and/or *Phakopsora meibomiae*.

Accordingly a further aspect of the present invention is a method of controlling rust diseases on soybean plants, which comprises applying to the soybean plants, the locus thereof or propagation material thereof a composition comprising a compound of formula (I).

Preferred is a method, which comprises applying to the soybean plants or to the locus thereof a composition comprising a compound of formula (I), preferably to the soybean plants.

Further preferred is a method, which comprises applying to the propagation material of the soybean plants a composition comprising a compound of formula (I).

The methods according to the invention, especially when a compound of formula (I) is used in combination with at least one compound (B) as described above, also allows good control of other harmful fungi frequently encountered in soybean plants. The most important fungal diseases in soybeans being *Phakopsora pachyrhizi*, *Microsphaera diffusa*, *Cercospora kikuchi*, *Cercospora sojina*, *Septoria glycines* and *Colletotrichum truncatum*, some of which comprise the so-called "late season disease complex", and furthermore *Rhizoctonia solani*, *Corynespora cassiicola*, *Sclerotinia sclerotiorum* and *Sclerosium rolfsii*.

Further characteristics of compositions comprising compounds of formula (I), their application methods to soybeans and their use rates are as described for compositions comprising compounds of formula (I) and additionally at least one component (B) as described above. Their application can be both before and after the infection of the soybean plants or parts thereof with the fungi. The treatment is preferably carried out prior to the infection. When a compound of formula (I) is used on its own, the application rates in the method according to the invention are as described above, e.g. typical are rates of 5 to 2000 g a.i./ha, particularly 10 to 1000 g a.i./ha, e.g. 50, 75, 100 or 200 g a.i./ha. Compounds of formula (I) can be applied to the soybean plants once or more than once during a growing season. For use in the method according to the invention, the compounds of formula (I) can be converted into the customary formulations described above, e.g. solutions, emulsions, suspensions, dusts, powders, pastes and granules. The use form will depend on the particular intended purpose; in each case, it should ensure a fine and even distribution of the compound of formula (I).

As described above for the term "useful plant", the term "soybean plant" includes all soybean plants and all varieties, including transgenic plants. The term "soybean plant" includes especially glyphosate tolerant soybean plants.

By "glyphosate tolerant" is meant that the plants for use in the methods are resistant to glyphosate application or tolerant of glyphosate. Glyphosate tolerant plants are made tolerant to glyphosate by conventional breeding or having a transgenic event that provides glyphosate resistance. Some examples of such preferred transgenic plants having transgenic events that confer glyphosate resistance are described in U.S. Pat. Nos. 5,914,451; 5,866,775; 5,804,425; 5,776,760; 5,633,435; 5,627,061; 5,463,175; 5,312,910; 5,310,667; 5,188,642; 5,145,783; 4,971,908 and 4,940,835. The use of "stacked" transgenic events in the plant is also contemplated.

Stacked transgenic events including additional herbicide-resistant traits such as resistance to HPPD-inhibitors, sulfonyl-ureas, glufosinate and bromoxynil are widely used and described in readily available resources. The stacked transgenic events may also be directed to other pesticide resistant traits, such as insecticide, nematicide, fungicide, etc resistance, which may be made by conventional breeding or introducing a transgenic event.

Lines of transgenic glyphosate tolerant crop plants contemplated for use in the methods of the present invention include, for example, Roundup Ready® Soybean 40-3-2.

A "transgenic plant" refers to a plant that contains genetic material not found (i.e. "exogenous") in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes. A transgenic plant may contain an expression vector or cassette. The expression cassette typically comprises a polypeptide-encoding sequence operably linked (i.e., under regulatory control of) to appropriate inducible or constitutive regulatory sequences that allow for the expression of the polypeptide. The expression cassette can be introduced into a plant by transformation or by breeding after transformation of a parent plant. As previously described a plant refers to a whole plant, including seedlings and mature plants, as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

If the soybean plants are glyphosate tolerant, then it is especially preferred that combinations of compounds of formula (I) and glyphosate are used. Above is given a general guidance to typical glyphosate application rates—as glyphosate is one of the compounds (B)—but the optimal rate to be used depends on many factors including the environment and should be determined under actual use conditions. Preferably, a rate of application of a glyphosate compound from about 400 g acid equivalent (ae)/ha to about 3400 g ae/ha of glyphosate is effective in controlling, preventing or treating a soybean rust pathogen, such as Asian soybean rust, in accordance with the method of the present invention. Yet more preferable are rates of application range from about 800 g ae/ha to 1700 g ae/ha. Generally, glyphosate-containing compositions can be applied, if applied only once, at a rate of 960 g ae/ha; if applied twice the rate can vary from 1200 to 1680 g ae/ha. When more than one application of glyphosate-containing compositions to the soybean plants are performed, it is not necessary that all glyphosate-containing compositions contain also a compound of formula (I). The rates and number of glyphosate-applications may vary according to the particular conditions. Preferably, glyphosate-containing compositions are applied three times with an application rate of 960, 720 and 400 g ae/ha respectively. In said embodiment of the invention, the present invention also provides a method for controlling undesired vegetation, such as harmful weeds, and controlling, preventing or treating soybean rust diseases in a field of glyphosate tolerant soybean plants. Preferably, the application or applications are timed for effective weed control and effective soybean rust control, prevention or treatment in the treated soybean plant. For example, without limitation, a glyphosate-containing composition is applied at a time when the application controls the weeds within the field; a second glyphosate-containing composition is applied at a time when the glyphospate tolerant soybean plants are either at risk of infection or have already been infected by a soybean rust disease, said second glyphosate-containing composition additionally comprises at least a compound of formula (I). Another application of the second glyphosate-containing composition can also be envisaged to further prevent infection.

The Examples which follow serve to illustrate the invention, "active ingredient" denotes a mixture of component (A) and component (B) in a specific mixing ratio. The same formulations can be used for compositions comprising only a compound of formula (I) as the active ingredient.

Formulation Examples

| Wettable powders | a) | b) |
|---|---|---|
| active ingredient [A):B) = 1:3(a), 1:1(b)] | 25% | 75% |
| sodium lignosulfonate | 5% | — |
| sodium lauryl sulfate | 3% | 5% |
| sodium diisobutylnaphthalenesulfonate | — | 10% |
| (7-8 mol of ethylene oxide) | | |
| highly dispersed silicic acid | 5% | 10% |
| kaolin | 62% | — |

The active ingredient is thoroughly mixed with the other formulation components and the mixture is thoroughly ground in a suitable mill, affording wettable powders that can be diluted with water to give suspensions of the desired concentration.

| Powders for dry seed treatment | a) | b) |
|---|---|---|
| active ingredient [A):B) = 1:3(a), 1:1(b)] | 25% | 75% |
| light mineral oil | 5% | 5% |
| highly dispersed silicic acid | 5% | — |
| kaolin | 65% | — |
| talc | — | 20 |

The active ingredient is thoroughly mixed with the other formulation components and the mixture is thoroughly ground in a suitable mill, affording powders that can be used directly for seed treatment.

Emulsifiable Concentrate

| | |
|---|---|
| active ingredient (A):B) = 1:6) | 10% |
| octylphenol polyethylene glycol ether | 3% |
| (4-5 mol of ethylene oxide) | |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Dustable powders | a) | b) |
|---|---|---|
| active ingredient [A):B) = 1:6(a), 1:10(b)] | 5% | 6% |
| talcum | 95% | — |
| kaolin | — | 94% |

Ready-for-use dusts are obtained by mixing the active ingredient with the carriers and grinding the mixture in a suitable mill. Such powders can also be used for dry dressings for seed.

| Extruded granules | % w/w |
|---|---|
| active ingredient (A):B) = 2:1) | 15% |
| sodium lignosulfonate | 2% |
| sodium alkyl naphthalene sulfonate | 1% |
| kaolin | 82% |

The active ingredient is mixed and ground with the other formulation components, and the mixture is moistened with water. The mixture is extruded and then dried in a stream of air.

Suspension Concentrate

| | |
|---|---|
| active ingredient (A):B) = 1:8) | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the other formulation components, giving a suspension concentrate which can be diluted in water at any desired rate. Using such dilutions, living plants as well as plant propagation material can be treated and protected against infestation by microorganisms, by spraying, pouring or immersion.

Flowable Concentrate for Seed Treatment

| | |
|---|---|
| active ingredient (A):B) = 1:8) | 40% |
| propylene glycol | 5% |
| copolymer butanol PO/EO | 2% |
| tristyrenephenole ethoxylate (with 10-20 moles EO) | 2% |
| 1,2-benzisothiazolin-3-one | 0.5% |
| monoazo-pigment calcium salt | 5% |
| silicone oil (in the form of a 75% emulsion in water) | 0.2% |
| water | 45.3% |

The finely ground active ingredient is intimately mixed with the other formulation components, giving a suspension concentrate which can be diluted further in water to be applied to seeds. Using such dilutions, propagation material can be treated and protected against infestation by microorganisms, by spraying, pouring or immersion.

Biological Examples

Example B-1

Action Against Asian Soybean Rust (*Phakopsora pachyrhizi*)—Leaf Disc Test

Whole soybean plants (variety brand Williams82) are treated with the recited active ingredients 4 weeks after planting. 1 day after spraying leaf disks are cut from the first trifoliate leaf. Five repetitions at each rate are conducted. The leaf disks are inoculated with *Phakopsora pachyrhizi* (Asian soybean rust) one day after treatment. Evaluation of the leaf disks is conducted fourteen days after inoculation and the mean percent infestation of the five repetitions is calculated. Standard EC100 formulations are used. The rates of the active ingredients used are given in Table B1 as g active ingredient (a.i.)/ha.

TABLE B1

Action against Asian soybean rust
% Control of *Phakopsora pachyrhizi*

| g.ai./ha | Cpd A-1.1 | Cpd A-1.2 | Cpd A-1.3 |
|---|---|---|---|
| 250 | 87 | 94 | 93 |
| 125 | 82 | 44 | 54 |

TABLE B1-continued

Action against Asian soybean rust
% Control of *Phakopsora pachyrhizi*

| g.ai./ha | Cpd A-1.1 | Cpd A-1.2 | Cpd A-1.3 |
|---|---|---|---|
| 62.5 | 36 | 54 | 36 |
| 31.25 | 36 | 39 | 36 |

Example B2

Fungicidal Action Against *Botrytis cinerea* (Gray Mould)

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is evaluated after 4 days. The expected fungicidal action is calculated according to the Colby method. The results are given in Tables B2:

Tables B2: Fungicidal Action Against *Botrytis cinerea*

TABLE B2.1

| Compound A-1.1 ppm | Azoxystrobin ppm | % activity | expected action (Colby) |
|---|---|---|---|
| 1.0000 | | 90 | |
| 0.5000 | | 50 | |
| 0.2500 | | 20 | |
| 0.1250 | | 20 | |
| | 2.0000 | 0 | |
| | 1.0000 | 0 | |
| | 0.5000 | 0 | |
| | 0.2500 | 0 | |
| | 0.1250 | 0 | |
| 1.0000 | 2.0000 | 100 | 90 |
| 1.0000 | 1.0000 | 100 | 90 |
| 1.0000 | 0.5000 | 100 | 90 |
| 0.5000 | 2.0000 | 100 | 50 |
| 0.5000 | 1.0000 | 100 | 50 |
| 0.5000 | 0.5000 | 100 | 50 |
| 0.5000 | 0.2500 | 90 | 50 |
| 0.5000 | 0.1250 | 70 | 50 |
| 0.2500 | 1.0000 | 100 | 20 |
| 0.2500 | 0.5000 | 100 | 20 |
| 0.2500 | 0.2500 | 70 | 20 |
| 0.2500 | 0.1250 | 50 | 20 |
| 0.1250 | 0.5000 | 90 | 20 |
| 0.1250 | 0.2500 | 50 | 20 |

TABLE B2.2

| Compound A-1.1 ppm | Picoxystrobin ppm | % activity | expected action (Colby) |
|---|---|---|---|
| 0.5000 | | 70 | |
| 0.2500 | | 50 | |
| 0.1250 | | 20 | |
| 0.0625 | | 20 | |
| | 2.0000 | 0 | |
| | 1.0000 | 0 | |
| | 0.5000 | 0 | |
| | 0.2500 | 0 | |
| | 0.1250 | 0 | |
| | 0.0625 | 0 | |
| 0.5000 | 2.0000 | 100 | 70 |
| 0.5000 | 1.0000 | 100 | 70 |
| 0.5000 | 0.5000 | 100 | 70 |
| 0.5000 | 0.2500 | 100 | 70 |
| 0.5000 | 0.1250 | 100 | 70 |

TABLE B2.2-continued

| Compound A-1.1 ppm | Picoxystrobin ppm | % activity | expected action (Colby) |
|---|---|---|---|
| 0.2500 | 1.0000 | 100 | 50 |
| 0.2500 | 0.5000 | 100 | 50 |
| 0.2500 | 0.2500 | 100 | 50 |
| 0.2500 | 0.1250 | 100 | 50 |
| 0.2500 | 0.0625 | 90 | 50 |
| 0.1250 | 0.5000 | 100 | 20 |
| 0.1250 | 0.2500 | 100 | 20 |
| 0.1250 | 0.1250 | 100 | 20 |
| 0.1250 | 0.0625 | 70 | 20 |
| 0.0625 | 0.2500 | 100 | 20 |
| 0.0625 | 0.1250 | 90 | 20 |
| 0.0625 | 0.0625 | 50 | 20 |

TABLE B2.3

| Compound A-1.1 ppm | Fludioxonil ppm | % activity | expected action (Colby) |
|---|---|---|---|
| 0.2500 | | 50 | |
| 0.1250 | | 20 | |
| 0.0625 | | 20 | |
| 0.0313 | | 0 | |
| 0.0156 | | 0 | |
| | 0.1250 | 90 | |
| | 0.0625 | 20 | |
| | 0.0313 | 0 | |
| 0.2500 | 0.0625 | 100 | 60 |
| 0.1250 | 0.0625 | 100 | 36 |
| 0.1250 | 0.0313 | 50 | 20 |
| 0.0625 | 0.0625 | 90 | 36 |
| 0.0625 | 0.0313 | 50 | 20 |
| 0.0313 | 0.1250 | 100 | 90 |
| 0.0313 | 0.0625 | 90 | 20 |
| 0.0156 | 0.0625 | 70 | 20 |

TABLE B2.4

| Compound A-1.2 ppm | Azoxystrobin ppm | % activity | expected action (Colby) |
|---|---|---|---|
| 2.0000 | | 70 | |
| 1.0000 | | 50 | |
| 0.5000 | | 20 | |
| 0.2500 | | 20 | |
| | 2.0000 | 0 | |
| | 1.0000 | 0 | |
| | 0.5000 | 0 | |
| | 0.2500 | 0 | |
| 2.0000 | 2.0000 | 100 | 70 |
| 2.0000 | 1.0000 | 100 | 70 |
| 2.0000 | 0.5000 | 100 | 70 |
| 1.0000 | 2.0000 | 100 | 50 |
| 1.0000 | 1.0000 | 100 | 50 |
| 1.0000 | 0.5000 | 100 | 50 |
| 1.0000 | 0.2500 | 70 | 50 |
| 0.5000 | 2.0000 | 100 | 20 |
| 0.5000 | 1.0000 | 100 | 20 |
| 0.5000 | 0.5000 | 100 | 20 |
| 0.5000 | 0.2500 | 50 | 20 |
| 0.2500 | 1.0000 | 90 | 20 |
| 0.2500 | 0.5000 | 70 | 20 |
| 0.2500 | 0.2500 | 50 | 20 |

TABLE B2.5

| Compound A-1.2 ppm | Picoxystrobin ppm | % activity | expected action (Colby) |
|---|---|---|---|
| 2.0000 | | 70 | |
| 1.0000 | | 50 | |
| 0.5000 | | 20 | |
| 0.2500 | | 20 | |
| 0.1250 | | 20 | |
| | 2.0000 | 0 | |
| | 1.0000 | 0 | |
| | 0.5000 | 0 | |
| | 0.2500 | 0 | |
| | 0.1250 | 0 | |
| 2.0000 | 2.0000 | 100 | 70 |
| 2.0000 | 1.0000 | 100 | 70 |
| 2.0000 | 0.5000 | 100 | 70 |
| 1.0000 | 2.0000 | 100 | 50 |
| 1.0000 | 1.0000 | 100 | 50 |
| 1.0000 | 0.5000 | 100 | 50 |
| 1.0000 | 0.2500 | 100 | 50 |
| 0.5000 | 2.0000 | 100 | 20 |
| 0.5000 | 1.0000 | 100 | 20 |
| 0.5000 | 0.5000 | 100 | 20 |
| 0.5000 | 0.2500 | 100 | 20 |
| 0.5000 | 0.1250 | 90 | 20 |
| 0.2500 | 1.0000 | 100 | 20 |
| 0.2500 | 0.5000 | 100 | 20 |
| 0.2500 | 0.2500 | 90 | 20 |
| 0.2500 | 0.1250 | 70 | 20 |
| 0.1250 | 0.5000 | 90 | 20 |
| 0.1250 | 0.2500 | 70 | 20 |
| 0.1250 | 0.1250 | 50 | 20 |

TABLE B2.6

| Compound A-1.2 ppm | Fludioxonil ppm | % activity | expected action (Colby) |
|---|---|---|---|
| 0.2500 | | 20 | |
| 0.1250 | | 20 | |
| 0.0313 | | 0 | |
| | 0.0625 | 20 | |
| 0.2500 | 0.0625 | 50 | 36 |
| 0.1250 | 0.0625 | 50 | 36 |
| 0.0313 | 0.0625 | 50 | 20 |

TABLE B2.7

| Compound A-1.2 ppm | Fenpropidin ppm | % activity | expected action (Colby) |
|---|---|---|---|
| 2.0000 | | 70 | |
| 1.0000 | | 50 | |
| 0.5000 | | 20 | |
| | 2.0000 | 0 | |
| | 1.0000 | 0 | |
| | 0.5000 | 0 | |
| 2.0000 | 2.0000 | 100 | 70 |
| 1.0000 | 2.0000 | 70 | 50 |
| 0.5000 | 2.0000 | 50 | 20 |
| 0.5000 | 1.0000 | 50 | 20 |
| 0.5000 | 0.5000 | 50 | 20 |

Example B3

Fungicidal Action Against *Septoria tritici* (Leaf Blotch)

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is evaluated after 4 days. The expected fungicidal action is calculated according to the Colby method. The results are given in Tables B3:

Tables B3: Fungicidal Action Against *Septoria tritici*:

TABLE B3.1

| Compound A-1.1 ppm | Azoxystrobin ppm | % activity | expected action (Colby) |
|---|---|---|---|
| 0.1250 |  | 50 |  |
| 0.0625 |  | 20 |  |
|  | 0.0625 | 70 |  |
| 0.1250 | 0.0625 | 100 | 85 |
| 0.0625 | 0.0625 | 90 | 76 |

TABLE B3.2

| Compound A-1.1 ppm | Picoxystrobin ppm | % activity | expected action (Colby) |
|---|---|---|---|
| 0.1250 |  | 50 |  |
| 0.0625 |  | 20 |  |
|  | 0.0313 | 70 |  |
|  | 0.0156 | 20 |  |
| 0.1250 | 0.0313 | 100 | 85 |
| 0.0625 | 0.0313 | 90 | 76 |
| 0.0625 | 0.0156 | 50 | 36 |

TABLE B3.3

| Compound A-1.2 ppm | Difenoconazole ppm | % activity | expected action (Colby) |
|---|---|---|---|
| 0.2500 |  | 20 |  |
| 0.0156 |  | 0 |  |
| 0.0078 |  | 0 |  |
|  | 0.0625 | 90 |  |
|  | 0.0313 | 50 |  |
| 0.2500 | 0.0625 | 70 | 92 |
| 0.0156 | 0.0313 | 70 | 50 |
| 0.0078 | 0.0313 | 70 | 50 |

TABLE B3.4

| Compound A-1.1 ppm | Fludioxonil ppm | % activity | expected action (Colby) |
|---|---|---|---|
| 0.5000 |  | 90 |  |
| 0.2500 |  | 70 |  |
|  | 0.1250 | 0 |  |
|  | 0.0625 | 0 |  |
| 0.5000 | 0.1250 | 100 | 90 |
| 0.2500 | 0.1250 | 90 | 70 |
| 0.2500 | 0.0625 | 90 | 70 |

TABLE B3.5

| Compound A-1.1 ppm | Cyprodinil ppm | % activity | expected action (Colby) |
|---|---|---|---|
| 0.2500 |  | 70 |  |
| 0.1250 |  | 50 |  |
|  | 2.0000 | 0 |  |
|  | 1.0000 | 0 |  |
|  | 0.5000 | 0 |  |
|  | 0.2500 | 0 |  |
|  | 0.1250 | 0 |  |
| 0.2500 | 1.0000 | 100 | 70 |
| 0.2500 | 0.5000 | 90 | 70 |
| 0.2500 | 0.2500 | 90 | 70 |
| 0.2500 | 0.1250 | 90 | 70 |
| 0.1250 | 0.5000 | 90 | 50 |

TABLE B3.6

| Compound A-1.2 ppm | Cyprodinil ppm | % activity | expected action (Colby) |
|---|---|---|---|
| 1.0000 |  | 70 |  |
| 0.5000 |  | 50 |  |
| 0.2500 |  | 20 |  |
| 0.1250 |  | 0 |  |
|  | 2.0000 | 0 |  |
|  | 1.0000 | 0 |  |
|  | 0.5000 | 0 |  |
| 1.0000 | 2.0000 | 100 | 70 |
| 1.0000 | 1.0000 | 100 | 70 |
| 1.0000 | 0.5000 | 90 | 70 |
| 0.5000 | 2.0000 | 100 | 50 |
| 0.5000 | 1.0000 | 100 | 50 |
| 0.2500 | 1.0000 | 100 | 20 |
| 0.2500 | 0.5000 | 70 | 20 |
| 0.1250 | 0.5000 | 70 | 0 |

TABLE B3.7

| Compound A-1.2 ppm | Mandipropamid ppm | % activity | expected action (Colby) |
|---|---|---|---|
| 0.2500 |  | 70 |  |
| 0.1250 |  | 50 |  |
|  | 0.5000 | 0 |  |
|  | 0.2500 | 0 |  |
|  | 0.1250 | 0 |  |
| 0.2500 | 0.5000 | 90 | 70 |
| 0.2500 | 0.2500 | 90 | 70 |
| 0.2500 | 0.1250 | 90 | 70 |
| 0.1250 | 0.1250 | 70 | 50 |

TABLE B3.8

| Compound A-1.1 ppm | Chlorothalonil ppm | % activity | expected action (Colby) |
|---|---|---|---|
| 0.5000 |  | 90 |  |
| 0.2500 |  | 70 |  |
| 0.1250 |  | 50 |  |
|  | 0.1250 | 0 |  |
|  | 0.0625 | 0 |  |
| 0.5000 | 0.1250 | 100 | 90 |
| 0.2500 | 0.1250 | 90 | 70 |
| 0.2500 | 0.0625 | 90 | 70 |
| 0.1250 | 0.1250 | 70 | 50 |

Example B4

Fungicidal Action Against *Alternaria solani* (Early Blight Tomato/Potato)

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is evaluated after 3 days. The expected fungicidal action is calculated according to the Colby method. The results are given in Tables B4:

Tables B4: Fungicidal Action Against *Alternaria solani*

TABLE B4.1

| Compound A-1.1 ppm | Azoxystrobin ppm | % activity | expected action (Colby) |
|---|---|---|---|
| 0.2500 | | 50 | |
| 0.0625 | | 50 | |
| 0.0313 | | 20 | |
| 0.0156 | | 20 | |
| 0.0078 | | 0 | |
| | 0.2500 | 50 | |
| | 0.0625 | 20 | |
| | 0.0313 | 20 | |
| | 0.0156 | 20 | |
| 0.2500 | 0.2500 | 90 | 75 |
| 0.0625 | 0.0625 | 70 | 60 |
| 0.0313 | 0.0625 | 50 | 36 |
| 0.0313 | 0.0313 | 50 | 36 |
| 0.0313 | 0.0156 | 50 | 36 |
| 0.0156 | 0.0625 | 50 | 36 |
| 0.0156 | 0.0313 | 50 | 36 |
| 0.0078 | 0.0313 | 50 | 20 |

TABLE B4.2

| Compound A-1.2 ppm | Azoxystrobin ppm | % activity | expected action (Colby) |
|---|---|---|---|
| 0.5000 | | 50 | |
| 0.1250 | | 20 | |
| 0.0625 | | 0 | |
| | 0.5000 | 50 | |
| | 0.2500 | 50 | |
| | 0.0313 | 20 | |
| 0.5000 | 0.5000 | 90 | 75 |
| 0.1250 | 0.5000 | 70 | 60 |
| 0.1250 | 0.0313 | 50 | 36 |
| 0.0625 | 0.2500 | 70 | 50 |
| 0.0625 | 0.0313 | 50 | 20 |

TABLE B4.3

| Compound A-1.1 ppm | Picoxystrobin ppm | % activity | expected action (Colby) |
|---|---|---|---|
| 0.1250 | | 50 | |
| 0.0625 | | 50 | |
| 0.0313 | | 20 | |
| 0.0156 | | 20 | |
| 0.0078 | | 0 | |
| | 0.0625 | 50 | |
| | 0.0313 | 20 | |
| | 0.0156 | 20 | |
| | 0.0078 | 0 | |
| 0.1250 | 0.0313 | 70 | 60 |
| 0.0625 | 0.0313 | 70 | 60 |
| 0.0625 | 0.0156 | 70 | 60 |
| 0.0313 | 0.0625 | 70 | 60 |
| 0.0313 | 0.0313 | 50 | 36 |
| 0.0313 | 0.0156 | 50 | 36 |
| 0.0313 | 0.0078 | 50 | 20 |
| 0.0156 | 0.0313 | 50 | 36 |
| 0.0078 | 0.0313 | 50 | 20 |

TABLE B4.4

| Compound A-1.2 ppm | Picoxystrobin ppm | % activity | expected action (Colby) |
|---|---|---|---|
| 0.5000 | | 50 | |
| 0.1250 | | 20 | |
| 0.0625 | | 0 | |
| 0.0313 | | 0 | |
| | 2.0000 | 50 | |
| | 0.5000 | 50 | |
| | 0.2500 | 50 | |
| | 0.1250 | 50 | |
| | 0.0625 | 50 | |
| 0.5000 | 2.0000 | 90 | 75 |
| 0.1250 | 0.5000 | 70 | 60 |
| 0.1250 | 0.2500 | 70 | 60 |
| 0.0625 | 0.1250 | 70 | 50 |
| 0.0625 | 0.2500 | 70 | 50 |
| 0.0313 | 0.1250 | 70 | 50 |
| 0.0313 | 0.0625 | 70 | 50 |

TABLE B4.5

| Compound A-1.1 ppm | Cyproconazole ppm | % activity | expected action (Colby) |
|---|---|---|---|
| 0.2500 | | 50 | |
| 0.1250 | | 50 | |
| | 0.5000 | 20 | |
| | 0.2500 | 0 | |
| | 0.1250 | 0 | |
| 0.2500 | 0.5000 | 70 | 60 |
| 0.2500 | 0.2500 | 70 | 50 |
| 0.1250 | 0.2500 | 70 | 50 |
| 0.1250 | 0.1250 | 70 | 50 |

TABLE B4.6

| Compound A-1.1 ppm | Fludioxonil ppm | % activity | expected action (Colby) |
|---|---|---|---|
| 0.2500 | | 50 | |
| 0.1250 | | 50 | |
| 0.0625 | | 50 | |
| 0.0313 | | 20 | |
| 0.0156 | | 20 | |
| | 0.2500 | 50 | |
| | 0.1250 | 50 | |
| | 0.0625 | 20 | |
| | 0.0313 | 0 | |
| | 0.0156 | 0 | |
| | 0.0078 | 0 | |
| 0.2500 | 0.1250 | 90 | 75 |
| 0.2500 | 0.0625 | 70 | 60 |
| 0.1250 | 0.2500 | 90 | 75 |
| 0.1250 | 0.0625 | 70 | 60 |
| 0.1250 | 0.0313 | 70 | 50 |
| 0.0625 | 0.0625 | 70 | 60 |
| 0.0313 | 0.1250 | 70 | 60 |
| 0.0313 | 0.0625 | 70 | 36 |
| 0.0313 | 0.0313 | 50 | 20 |
| 0.0313 | 0.0156 | 50 | 20 |
| 0.0313 | 0.0078 | 50 | 20 |
| 0.0156 | 0.0625 | 50 | 36 |

TABLE B4.7

| Compound A-1.2 ppm | Fludioxonil ppm | % activity | expected action (Colby) |
|---|---|---|---|
| 0.5000 | | 50 | |
| 0.2500 | | 50 | |
| 0.1250 | | 20 | |
| 0.0625 | | 20 | |
| 0.0313 | | 0 | |
| | 0.5000 | 70 | |
| | 0.2500 | 50 | |
| | 0.1250 | 20 | |

TABLE B4.7-continued

| Compound A-1.2 ppm | Fludioxonil ppm | % activity | expected action (Colby) |
|---|---|---|---|
| 0.5000 | 0.2500 | 90 | 75 |
| 0.5000 | 0.1250 | 70 | 60 |
| 0.2500 | 0.2500 | 90 | 75 |
| 0.2500 | 0.1250 | 70 | 60 |
| 0.1250 | 0.5000 | 90 | 76 |
| 0.1250 | 0.2500 | 90 | 60 |
| 0.1250 | 0.1250 | 50 | 36 |
| 0.0625 | 0.2500 | 70 | 60 |
| 0.0625 | 0.1250 | 50 | 36 |
| 0.0313 | 0.1250 | 50 | 20 |

TABLE B4.8

| Compound A-1.1 ppm | Cyprodinil ppm | % activity | expected action (Colby) |
|---|---|---|---|
| 0.2500 |  | 50 |  |
| 0.1250 |  | 50 |  |
| 0.0625 |  | 50 |  |
|  | 0.2500 | 50 |  |
| 0.2500 | 0.2500 | 90 | 75 |
| 0.1250 | 0.2500 | 90 | 75 |
| 0.0625 | 0.2500 | 90 | 75 |

TABLE B4.9

| Compound A-1.1 ppm | Fenpropidin ppm | % activity | expected action (Colby) |
|---|---|---|---|
| 0.2500 |  | 50 |  |
| 0.1250 |  | 50 |  |
| 0.0313 |  | 20 |  |
|  | 1.0000 | 0 |  |
|  | 0.5000 | 0 |  |
|  | 0.2500 | 0 |  |
|  | 0.1250 | 0 |  |
| 0.2500 | 1.0000 | 70 | 50 |
| 0.2500 | 0.5000 | 70 | 50 |
| 0.2500 | 0.2500 | 70 | 50 |
| 0.1250 | 0.5000 | 70 | 50 |
| 0.0313 | 0.1250 | 50 | 20 |

Example B5

Fungicidal Action Against *Pseudocercosporella herpotrichoides* (Syn. *Tapesia yallundae*), Eye Spot of Cereals Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is evaluated after 4 days. The expected fungicidal action is calculated according to the Colby method. The results are given in Tables B5:

Tables B5: Fungicidal Action Against *Pseudocercosporella herpotrichoides*:

TABLE B5.1

| Compound A-1.1 ppm | Picoxystrobin ppm | % activity | expected action (Colby) |
|---|---|---|---|
| 0.0625 |  | 70 |  |
| 0.0313 |  | 50 |  |
| 0.0156 |  | 20 |  |
| 0.0078 |  | 0 |  |
|  | 0.2500 | 50 |  |
|  | 0.1250 | 50 |  |
|  | 0.0625 | 50 |  |
|  | 0.0313 | 50 |  |
|  | 0.0156 | 20 |  |
|  | 0.0078 | 0 |  |
| 0.0625 | 0.2500 | 100 | 85 |
| 0.0625 | 0.1250 | 100 | 85 |
| 0.0625 | 0.0156 | 90 | 76 |
| 0.0313 | 0.1250 | 100 | 75 |
| 0.0313 | 0.0625 | 90 | 75 |
| 0.0313 | 0.0313 | 90 | 75 |
| 0.0313 | 0.0156 | 70 | 60 |
| 0.0156 | 0.0625 | 90 | 60 |
| 0.0156 | 0.0313 | 90 | 60 |
| 0.0156 | 0.0078 | 50 | 20 |
| 0.0078 | 0.0313 | 70 | 50 |
| 0.0078 | 0.0156 | 50 | 20 |

TABLE B5.2

| Compound A-1.2 ppm | Picoxystrobin ppm | % activity | expected action (Colby) |
|---|---|---|---|
| 0.2500 |  | 50 |  |
| 0.1250 |  | 20 |  |
| 0.0625 |  | 0 |  |
| 0.0313 |  | 0 |  |
| 0.0156 |  | 0 |  |
|  | 1.0000 | 70 |  |
|  | 0.5000 | 50 |  |
|  | 0.2500 | 50 |  |
|  | 0.1250 | 50 |  |
|  | 0.0625 | 50 |  |
| 0.2500 | 1.0000 | 100 | 85 |
| 0.2500 | 0.5000 | 100 | 75 |
| 0.2500 | 0.2500 | 90 | 75 |
| 0.2500 | 0.1250 | 100 | 75 |
| 0.2500 | 0.0625 | 90 | 75 |
| 0.1250 | 0.5000 | 90 | 60 |
| 0.1250 | 0.2500 | 90 | 60 |
| 0.1250 | 0.1250 | 90 | 60 |
| 0.1250 | 0.0625 | 70 | 60 |
| 0.0625 | 0.2500 | 90 | 50 |
| 0.0625 | 0.1250 | 90 | 50 |
| 0.0625 | 0.0625 | 70 | 50 |
| 0.0313 | 0.1250 | 70 | 50 |
| 0.0313 | 0.0625 | 70 | 50 |
| 0.0156 | 0.0625 | 70 | 50 |

TABLE B5.3

| Compound A-1.2 ppm | Difenoconazole ppm | % activity | expected action (Colby) |
|---|---|---|---|
| 0.2500 |  | 20 |  |
| 0.1250 |  | 0 |  |
| 0.0625 |  | 0 |  |
|  | 0.1250 | 50 |  |
| 0.2500 | 0.1250 | 70 | 60 |
| 0.1250 | 0.1250 | 70 | 50 |
| 0.0625 | 0.1250 | 70 | 50 |

TABLE B5.4

| Compound A-1.2 ppm | Cyproconazole ppm | % activity | expected action (Colby) |
|---|---|---|---|
| 0.1250 | | 20 | |
| 0.0625 | | 0 | |
| | 0.2500 | 70 | |
| 0.1250 | 0.2500 | 90 | 76 |
| 0.0625 | 0.2500 | 90 | 70 |

TABLE B5.5

| Compound A-1.1 ppm | Epoxiconazole ppm | % activity | expected action (Colby) |
|---|---|---|---|
| 0.0313 | | 50 | |
| 0.0156 | | 20 | |
| | 0.1250 | 70 | |
| | 0.0625 | 20 | |
| | 0.0313 | 0 | |
| 0.0313 | 0.1250 | 100 | 85 |
| 0.0313 | 0.0625 | 70 | 60 |
| 0.0156 | 0.0313 | 50 | 20 |
| 0.0156 | 0.0625 | 70 | 36 |

TABLE B5.6

| Compound A-1.2 ppm | Epoxiconazole ppm | % activity | expected action (Colby) |
|---|---|---|---|
| 0.0625 | | 0 | |
| 0.0313 | | 0 | |
| 0.0156 | | 0 | |
| 0.0078 | | 0 | |
| 0.0039 | | 0 | |
| | 0.2500 | 90 | |
| | 0.1250 | 70 | |
| | 0.0625 | 50 | |
| | 0.0313 | 20 | |
| | 0.0156 | 0 | |
| 0.0625 | 0.2500 | 100 | 90 |
| 0.0313 | 0.1250 | 100 | 70 |
| 0.0156 | 0.0625 | 70 | 50 |
| 0.0078 | 0.0313 | 50 | 20 |
| 0.0039 | 0.0156 | 50 | 0 |

TABLE B5.7

| Compound A-1.1 ppm | Fludioxonil ppm | % activity | expected action (Colby) |
|---|---|---|---|
| 0.0625 | | 70 | |
| 0.0313 | | 20 | |
| | 0.2500 | 20 | |
| | 0.0156 | 0 | |
| | 0.0078 | 0 | |
| 0.0625 | 0.2500 | 90 | 76 |
| 0.0625 | 0.0156 | 90 | 70 |
| 0.0313 | 0.0156 | 50 | 20 |
| 0.0313 | 0.0078 | 50 | 20 |

TABLE B5.8

| Compound A-1.2 ppm | Fludioxonil ppm | % activity | expected action (Colby) |
|---|---|---|---|
| 0.5000 | | 70 | |
| 0.2500 | | 20 | |
| | 2.0000 | 20 | |
| | 1.0000 | 20 | |
| | 0.5000 | 20 | |
| | 0.2500 | 20 | |

TABLE B5.8-continued

| Compound A-1.2 ppm | Fludioxonil ppm | % activity | expected action (Colby) |
|---|---|---|---|
| 0.5000 | 2.0000 | 100 | 76 |
| 0.5000 | 1.0000 | 100 | 76 |
| 0.5000 | 0.5000 | 90 | 76 |
| 0.2500 | 1.0000 | 70 | 36 |
| 0.2500 | 0.5000 | 70 | 36 |
| 0.2500 | 0.2500 | 50 | 36 |

TABLE B5.9

| Compound A-1.1 ppm | Cyprodinil ppm | % activity | expected action (Colby) |
|---|---|---|---|
| 0.0313 | | 50 | |
| 0.0156 | | 0 | |
| 0.0078 | | 0 | |
| 0.0039 | | 0 | |
| | 0.0313 | 70 | |
| | 0.0156 | 20 | |
| 0.0313 | 0.0156 | 70 | 60 |
| 0.0156 | 0.0313 | 90 | 70 |
| 0.0156 | 0.0156 | 50 | 20 |
| 0.0078 | 0.0156 | 50 | 20 |
| 0.0039 | 0.0156 | 50 | 20 |

TABLE B5.10

| Compound A-1.1 ppm | Fenpropidin ppm | % activity | expected action (Colby) |
|---|---|---|---|
| 0.0625 | | 70 | |
| 0.0313 | | 50 | |
| 0.0156 | | 20 | |
| | 0.2500 | 0 | |
| | 0.1250 | 0 | |
| | 0.0625 | 0 | |
| | 0.0313 | 0 | |
| | 0.0156 | 0 | |
| 0.0625 | 0.2500 | 90 | 70 |
| 0.0625 | 0.1250 | 90 | 70 |
| 0.0625 | 0.0625 | 90 | 70 |
| 0.0625 | 0.0313 | 90 | 70 |
| 0.0625 | 0.0156 | 90 | 70 |
| 0.0313 | 0.0156 | 70 | 50 |
| 0.0156 | 0.0625 | 50 | 20 |
| 0.0156 | 0.0313 | 50 | 20 |

TABLE B5.11

| Compound A-1.1 ppm | Chlorothalonil ppm | % activity | expected action (Colby) |
|---|---|---|---|
| 0.0313 | | 20 | |
| 0.0156 | | 20 | |
| 0.0078 | | 0 | |
| | 0.0313 | 50 | |
| | 0.0156 | 0 | |
| 0.0313 | 0.0313 | 70 | 60 |
| 0.0313 | 0.0156 | 50 | 20 |
| 0.0156 | 0.0313 | 70 | 60 |
| 0.0078 | 0.0313 | 70 | 50 |

TABLE B5.12

| Compound A-1.2 ppm | Chlorothalonil ppm | % activity | expected action (Colby) |
|---|---|---|---|
| 0.1250 | | 0 | |
| 0.0625 | | 0 | |

TABLE B5.12-continued

| Compound A-1.2 ppm | Chlorothalonil ppm | % activity | expected action (Colby) |
|---|---|---|---|
| 0.0313 | | 0 | |
| 0.0156 | | 0 | |
| | 0.1250 | 90 | |
| | 0.0313 | 50 | |
| 0.1250 | 0.1250 | 100 | 90 |
| 0.1250 | 0.0313 | 90 | 50 |
| 0.0625 | 0.1250 | 100 | 90 |
| 0.0625 | 0.0313 | 70 | 50 |
| 0.0313 | 0.1250 | 100 | 90 |
| 0.0313 | 0.0313 | 70 | 50 |
| 0.0156 | 0.0313 | 70 | 50 |

Example B6

Fungicidal Action Against *Pyrenophora teres* (Net Blotch)

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is evaluated after 4 days. The expected fungicidal action is calculated according to the Colby method. The results are given in Tables B6:

Tables B6: Fungicidal Action Against *Pyrenophora teres*:

TABLE B6.1

| Compound A-1.1 ppm | Azoxystrobin ppm | % activity | expected action (Colby) |
|---|---|---|---|
| 0.0625 | | 20 | |
| 0.0313 | | 20 | |
| 0.0156 | | 0 | |
| 0.0078 | | 0 | |
| | 0.1250 | 70 | |
| | 0.0625 | 50 | |
| | 0.0313 | 20 | |
| 0.0625 | 0.1250 | 90 | 76 |
| 0.0625 | 0.0313 | 50 | 36 |
| 0.0313 | 0.0625 | 70 | 60 |
| 0.0313 | 0.0313 | 50 | 36 |
| 0.0156 | 0.0625 | 70 | 50 |
| 0.0156 | 0.0313 | 50 | 20 |
| 0.0313 | 0.1250 | 90 | 76 |
| 0.0078 | 0.0313 | 50 | 20 |

TABLE B6.2

| Compound A-1.2 ppm | Azoxystrobin ppm | % activity | expected action (Colby) |
|---|---|---|---|
| 0.2500 | | 20 | |
| 0.1250 | | 20 | |
| 0.0313 | | 0 | |
| 0.0156 | | 0 | |
| 0.0078 | | 0 | |
| | 0.0625 | 50 | |
| | 0.0313 | 20 | |
| 0.2500 | 0.0625 | 70 | 60 |
| 0.1250 | 0.0313 | 50 | 36 |
| 0.0313 | 0.0625 | 70 | 50 |
| 0.0156 | 0.0625 | 70 | 50 |
| 0.0156 | 0.0313 | 50 | 20 |
| 0.0078 | 0.0313 | 50 | 20 |

TABLE B6.3

| Compound A-1.1 ppm | Picoxystrobin ppm | % activity | expected action (Colby) |
|---|---|---|---|
| 0.2500 | | 50 | |
| 0.1250 | | 20 | |
| 0.0625 | | 20 | |
| 0.0313 | | 20 | |
| 0.0156 | | 20 | |
| | 0.0625 | 70 | |
| | 0.0313 | 50 | |
| 0.2500 | 0.0625 | 100 | 85 |
| 0.1250 | 0.0625 | 100 | 76 |
| 0.1250 | 0.0313 | 90 | 60 |
| 0.0625 | 0.0625 | 100 | 76 |
| 0.0625 | 0.0313 | 70 | 60 |
| 0.0313 | 0.0625 | 90 | 76 |
| 0.0313 | 0.0313 | 70 | 60 |
| 0.0156 | 0.0625 | 90 | 76 |
| 0.0156 | 0.0313 | 70 | 60 |

TABLE B6.4

| Compound A-1.1 ppm | Difenoconazole ppm | % activity | expected action (Colby) |
|---|---|---|---|
| 1.0000 | | 70 | |
| 0.5000 | | 50 | |
| 0.2500 | | 50 | |
| 0.1250 | | 20 | |
| 0.0625 | | 20 | |
| 0.0313 | | 20 | |
| 0.0156 | | 20 | |
| | 1.0000 | 70 | |
| | 0.2500 | 50 | |
| | 0.1250 | 50 | |
| | 0.0625 | 20 | |
| 1.0000 | 0.2500 | 100 | 85 |
| 0.5000 | 1.0000 | 100 | 85 |
| 0.5000 | 0.2500 | 90 | 75 |
| 0.5000 | 0.1250 | 90 | 75 |
| 0.2500 | 0.2500 | 90 | 75 |
| 0.2500 | 0.1250 | 90 | 75 |
| 0.2500 | 0.0625 | 70 | 60 |
| 0.1250 | 0.2500 | 90 | 60 |
| 0.1250 | 0.1250 | 90 | 60 |
| 0.1250 | 0.0625 | 70 | 36 |
| 0.0625 | 0.2500 | 70 | 60 |
| 0.0625 | 0.1250 | 70 | 60 |
| 0.0625 | 0.0625 | 70 | 36 |
| 0.0313 | 0.1250 | 70 | 60 |
| 0.0313 | 0.0625 | 50 | 36 |
| 0.0156 | 0.0625 | 50 | 36 |

TABLE B6.5

| Compound A-1.2 ppm | Difenoconazole ppm | % activity | expected action (Colby) |
|---|---|---|---|
| 0.2500 | | 20 | |
| 0.1250 | | 20 | |
| | 1.0000 | 70 | |
| | 0.5000 | 70 | |
| | 0.1250 | 50 | |
| | 0.0625 | 20 | |
| 0.2500 | 1.0000 | 90 | 76 |
| 0.2500 | 0.5000 | 90 | 76 |
| 0.2500 | 0.0625 | 50 | 36 |
| 0.1250 | 0.1250 | 70 | 60 |

TABLE B6.6

| Compound A-1.2 ppm | Propiconazole ppm | % activity | expected action (Colby) |
|---|---|---|---|
| 1.0000 | | 50 | |
| 0.5000 | | 50 | |
| 0.2500 | | 20 | |
| | 2.0000 | 50 | |
| | 1.0000 | 20 | |
| 1.0000 | 2.0000 | 90 | 75 |
| 0.5000 | 2.0000 | 90 | 75 |
| 0.5000 | 1.0000 | 70 | 60 |
| 0.2500 | 1.0000 | 50 | 36 |

TABLE B6.7

| Compound A-1.1 ppm | Epoxiconazole ppm | % activity | expected action (Colby) |
|---|---|---|---|
| 0.2500 | | 50 | |
| 0.1250 | | 50 | |
| 0.0625 | | 20 | |
| 0.0313 | | 20 | |
| | 0.5000 | 50 | |
| | 0.2500 | 20 | |
| | 0.1250 | 20 | |
| 0.2500 | 0.5000 | 90 | 75 |
| 0.2500 | 0.2500 | 70 | 60 |
| 0.1250 | 0.5000 | 90 | 75 |
| 0.1250 | 0.2500 | 70 | 60 |
| 0.0625 | 0.2500 | 70 | 36 |
| 0.0625 | 0.1250 | 50 | 36 |
| 0.0313 | 0.1250 | 70 | 36 |

TABLE B6.8

| Compound A-1.2 ppm | Epoxiconazole ppm | % activity | expected action (Colby) |
|---|---|---|---|
| 1.0000 | | 50 | |
| 0.5000 | | 50 | |
| 0.2500 | | 20 | |
| 0.1250 | | 20 | |
| 0.0625 | | 0 | |
| | 1.0000 | 70 | |
| | 0.5000 | 50 | |
| | 0.2500 | 50 | |
| | 0.1250 | 20 | |
| 1.0000 | 0.5000 | 90 | 75 |
| 0.5000 | 0.5000 | 90 | 75 |
| 0.2500 | 1.0000 | 90 | 76 |
| 0.2500 | 0.5000 | 90 | 60 |
| 0.2500 | 0.2500 | 70 | 60 |
| 0.2500 | 0.1250 | 50 | 36 |
| 0.1250 | 0.5000 | 70 | 60 |
| 0.1250 | 0.2500 | 70 | 60 |
| 0.0625 | 0.2500 | 70 | 50 |

TABLE B6.9

| Compound A-1.1 ppm | Fludioxonil ppm | % activity | expected action (Colby) |
|---|---|---|---|
| 0.5000 | | 50 | |
| 0.2500 | | 50 | |
| 0.1250 | | 20 | |
| 0.0625 | | 20 | |
| 0.0313 | | 20 | |
| 0.0156 | | 0 | |
| | 0.1250 | 70 | |
| | 0.0625 | 20 | |
| 0.5000 | 0.1250 | 100 | 85 |
| 0.2500 | 0.1250 | 100 | 85 |
| 0.1250 | 0.1250 | 100 | 76 |

TABLE B6.9-continued

| Compound A-1.1 ppm | Fludioxonil ppm | % activity | expected action (Colby) |
|---|---|---|---|
| 0.1250 | 0.0625 | 50 | 36 |
| 0.0625 | 0.1250 | 90 | 76 |
| 0.0313 | 0.1250 | 90 | 76 |
| 0.0313 | 0.0625 | 20 | 36 |
| 0.0156 | 0.0625 | 90 | 20 |

TABLE B6.10

| Compound A-1.2 ppm | Fludioxonil ppm | % activity | expected action (Colby) |
|---|---|---|---|
| 0.2500 | | 20 | |
| 0.1250 | | 20 | |
| 0.0625 | | 20 | |
| 0.0313 | | 0 | |
| | 0.1250 | 70 | |
| 0.2500 | 0.1250 | 90 | 76 |
| 0.1250 | 0.1250 | 90 | 76 |
| 0.0625 | 0.1250 | 90 | 76 |
| 0.0313 | 0.1250 | 100 | 70 |

TABLE B6.11

| Compound A-1.2 ppm | Cyprodinil ppm | % activity | expected action (Colby) |
|---|---|---|---|
| 0.2500 | | 20 | |
| 0.1250 | | 20 | |
| 0.0625 | | 20 | |
| 0.0313 | | 0 | |
| | 0.2500 | 50 | |
| | 0.1250 | 50 | |
| | 0.0625 | 20 | |
| | 0.0313 | 20 | |
| 0.2500 | 0.0625 | 50 | 36 |
| 0.1250 | 0.0625 | 50 | 36 |
| 0.1250 | 0.0313 | 50 | 36 |
| 0.0625 | 0.2500 | 70 | 60 |
| 0.0625 | 0.0625 | 50 | 36 |
| 0.0313 | 0.1250 | 70 | 50 |
| 0.0313 | 0.0625 | 50 | 20 |

TABLE B6.12

| Compound A-1.1 ppm | Fenpropidin ppm | % activity | expected action (Colby) |
|---|---|---|---|
| 2.0000 | | 70 | |
| 0.1250 | | 20 | |
| | 2.0000 | 0 | |
| | 0.5000 | 0 | |
| | 0.2500 | 0 | |
| | 0.1250 | 0 | |
| | 0.0625 | 0 | |
| 2.0000 | 2.0000 | 90 | 70 |
| 0.1250 | 0.5000 | 50 | 20 |
| 0.1250 | 0.2500 | 50 | 20 |
| 0.1250 | 0.1250 | 50 | 20 |
| 0.1250 | 0.0625 | 50 | 20 |

TABLE B6.13

| Compound A-1.1 ppm | Mandipropamid ppm | % activity | expected action (Colby) |
|---|---|---|---|
| 0.2500 | | 50 | |
| 0.1250 | | 20 | |
| | 1.0000 | 0 | |
| | 0.5000 | 0 | |

TABLE B6.13-continued

| Compound A-1.1 ppm | Mandipropamid ppm | % activity | expected action (Colby) |
|---|---|---|---|
| 0.2500 | 1.0000 | 70 | 50 |
| 0.1250 | 0.5000 | 50 | 20 |

TABLE B6.14

| Compound A-1.1 ppm | Chlorothalonil ppm | % activity | expected action (Colby) |
|---|---|---|---|
| 2.0000 |  | 70 |  |
| 1.0000 |  | 70 |  |
| 0.5000 |  | 70 |  |
| 0.2500 |  | 50 |  |
| 0.1250 |  | 20 |  |
|  | 0.5000 | 20 |  |
| 2.0000 | 0.5000 | 100 | 76 |
| 1.0000 | 0.5000 | 100 | 76 |
| 0.5000 | 0.5000 | 100 | 76 |
| 0.2500 | 0.5000 | 100 | 60 |
| 0.1250 | 0.5000 | 100 | 36 |

TABLE B6.15

| Compound A-1.2 ppm | Chlorothalonil ppm | % activity | expected action (Colby) |
|---|---|---|---|
| 2.0000 |  | 70 |  |
| 1.0000 |  | 50 |  |
| 0.5000 |  | 50 |  |
| 0.2500 |  | 20 |  |
| 0.1250 |  | 20 |  |
|  | 0.5000 | 20 |  |
|  | 0.2500 | 0 |  |
| 2.0000 | 0.5000 | 90 | 76 |
| 1.0000 | 0.5000 | 90 | 60 |
| 0.5000 | 0.5000 | 100 | 60 |
| 0.2500 | 0.5000 | 100 | 36 |
| 0.2500 | 0.2500 | 50 | 20 |
| 0.1250 | 0.5000 | 100 | 36 |

Example B7

Fungicidal Action Against *Gaeumannomyces graminis* (Take-all of Cereals)

Mycelial fragments of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is evaluated after 4 days. The results are given in Tables B7:

Tables B7: Fungicidal Action Against *Gaeumannomyces graminis*:

TABLE B7.1

| Compound A-1.1 ppm | Cyproconazole ppm | % activity | expected action (Colby) |
|---|---|---|---|
| 0.0156 |  | 50 |  |
| 0.0078 |  | 20 |  |
|  | 0.0625 | 20 |  |
|  | 0.0313 | 0 |  |
|  | 0.0039 | 0 |  |
| 0.0156 | 0.0625 | 90 | 60 |
| 0.0156 | 0.0313 | 90 | 50 |
| 0.0156 | 0.0039 | 90 | 50 |
| 0.0078 | 0.0039 | 50 | 20 |

TABLE B7.2

| Compound A-1.1 ppm | Difenoconazole ppm | % activity | expected action (Colby) |
|---|---|---|---|
| 0.0156 |  | 50 |  |
|  | 0.0625 | 0 |  |
|  | 0.0313 | 0 |  |
|  | 0.0156 | 0 |  |
|  | 0.0039 | 0 |  |
| 0.0156 | 0.0625 | 70 | 50 |
| 0.0156 | 0.0313 | 70 | 50 |
| 0.0156 | 0.0156 | 70 | 50 |
| 0.0156 | 0.0039 | 90 | 50 |

TABLE B7.3

| Compound A-1.1 ppm | Propiconazole ppm | % activity | expected action (Colby) |
|---|---|---|---|
| 0.0156 |  | 70 |  |
|  | 0.0625 | 0 |  |
|  | 0.0078 | 0 |  |
|  | 0.0039 | 0 |  |
| 0.0156 | 0.0625 | 90 | 70 |
| 0.0156 | 0.0078 | 90 | 70 |
| 0.0156 | 0.0039 | 90 | 70 |

TABLE B7.4

| Compound A-1.1 ppm | Mandipropamid ppm | % activity | expected action (Colby) |
|---|---|---|---|
| 0.0156 |  | 70 |  |
| 0.0078 |  | 0 |  |
|  | 0.0625 | 0 |  |
|  | 0.0313 | 0 |  |
|  | 0.0078 | 0 |  |
|  | 0.0039 | 0 |  |
| 0.0156 | 0.0625 | 90 | 70 |
| 0.0156 | 0.0313 | 90 | 70 |
| 0.0156 | 0.0078 | 100 | 70 |
| 0.0078 | 0.0039 | 100 | 0 |

TABLE B7.5

| Compound A-1.2 ppm | Prothioconazole ppm | % activity | expected action (Colby) |
|---|---|---|---|
| 0.2500 |  | 20 |  |
| 0.1250 |  | 0 |  |
| 0.0625 |  | 0 |  |
| 0.0156 |  | 0 |  |
|  | 0.5000 | 90 |  |
|  | 0.2500 | 90 |  |
|  | 0.0625 | 50 |  |
| 0.2500 | 0.0625 | 70 | 60 |
| 0.1250 | 0.5000 | 100 | 90 |
| 0.1250 | 0.2500 | 100 | 90 |
| 0.0625 | 0.2500 | 100 | 90 |
| 0.0625 | 0.0625 | 90 | 50 |
| 0.0156 | 0.0625 | 90 | 50 |

TABLE B7.6

| Compound A-1.2 ppm | Tebuconazole ppm | % activity | expected action (Colby) |
|---|---|---|---|
| 0.2500 |  | 20 |  |
| 0.1250 |  | 0 |  |
| 0.0313 |  | 0 |  |
|  | 0.1250 | 50 |  |
| 0.2500 | 0.1250 | 90 | 60 |
| 0.1250 | 0.1250 | 70 | 50 |
| 0.0313 | 0.1250 | 90 | 50 |

TABLE B7.7

| Compound A-1.2 ppm | Fenpropimorph ppm | % activity | expected action (Colby) |
|---|---|---|---|
| 0.5000 |  | 70 |  |
|  | 2.0000 | 20 |  |
|  | 1.0000 | 0 |  |
|  | 0.5000 | 0 |  |
|  | 0.2500 | 0 |  |
| 0.5000 | 2.0000 | 90 | 76 |
| 0.5000 | 1.0000 | 90 | 70 |
| 0.5000 | 0.5000 | 90 | 70 |
| 0.5000 | 0.2500 | 90 | 70 |

TABLE B7.8

| Compound A-1.2 ppm | Fluopyram ppm | % activity | expected action (Colby) |
|---|---|---|---|
| 0.5000 |  | 90 |  |
| 0.2500 |  | 0 |  |
|  | 2.0000 | 0 |  |
|  | 1.0000 | 0 |  |
|  | 0.5000 | 0 |  |
|  | 0.2500 | 0 |  |
|  | 0.1250 | 0 |  |
| 0.5000 | 2.0000 | 100 | 90 |
| 0.5000 | 1.0000 | 100 | 90 |
| 0.5000 | 0.5000 | 100 | 90 |
| 0.5000 | 0.1250 | 100 | 90 |
| 0.2500 | 0.5000 | 50 | 0 |
| 0.2500 | 0.2500 | 90 | 0 |

TABLE B7.9

| Compound A-1.1 ppm | Fluopyram ppm | % activity | expected action (Colby) |
|---|---|---|---|
| 0.0156 |  | 70 |  |
|  | 0.0313 | 0 |  |
|  | 0.0156 | 0 |  |
|  | 0.0078 | 0 |  |
|  | 0.0039 | 0 |  |
| 0.0156 | 0.0313 | 90 | 70 |
| 0.0156 | 0.0156 | 100 | 70 |
| 0.0156 | 0.0078 | 90 | 70 |
| 0.0156 | 0.0039 | 90 | 70 |

Example B8

**Fungicidal Action Against *Cercospora arachidicola* (Syn. *Mycosphaerella arachidis*), Brown Leaf Spot of Groundnut (Peanut)**

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is evaluated after 7 days. The results are given in Tables B8:

Tables B8: Fungicidal Action Against *Cercospora arachidicola*:

TABLE B8.1

| Compound A-1.2 ppm | Propiconazole ppm | % activity | expected action (Colby) |
|---|---|---|---|
| 0.1250 |  | 20 |  |
| 0.0313 |  | 0 |  |
|  | 0.1250 | 90 |  |
|  | 0.0625 | 70 |  |
|  | 0.0313 | 20 |  |
| 0.0313 | 0.1250 | 100 | 90 |
| 0.0313 | 0.0625 | 90 | 70 |
| 0.1250 | 0.0313 | 50 | 36 |

TABLE B8.2

| Compound A-1.1 ppm | Mandipropamid ppm | % activity | expected action (Colby) |
|---|---|---|---|
| 0.0156 |  | 20 |  |
| 0.0078 |  | 0 |  |
|  | 0.0078 | 0 |  |
|  | 0.0039 | 0 |  |
| 0.0156 | 0.0039 | 50 | 20 |
| 0.0156 | 0.0078 | 50 | 20 |
| 0.0078 | 0.0039 | 70 | 0 |

TABLE B8.3

| Compound A-1.2 ppm | Prothioconazole ppm | % activity | expected action (Colby) |
|---|---|---|---|
| 0.0625 |  | 0 |  |
| 0.0313 |  | 0 |  |
| 0.0156 |  | 0 |  |
|  | 0.0625 | 70 |  |
| 0.0625 | 0.0625 | 90 | 70 |
| 0.0313 | 0.0625 | 90 | 70 |
| 0.0156 | 0.0625 | 90 | 70 |

TABLE B8.4

| Compound A-1.2 ppm | Fenpropimorph ppm | % activity | expected action (Colby) |
|---|---|---|---|
| 0.2500 |  | 70 |  |
| 0.1250 |  | 20 |  |
| 0.0625 |  | 0 |  |
|  | 0.5000 | 50 |  |
|  | 0.2500 | 20 |  |
|  | 0.1250 | 0 |  |
|  | 0.0625 | 0 |  |
| 0.2500 | 0.0625 | 90 | 70 |
| 0.1250 | 0.5000 | 70 | 60 |
| 0.1250 | 0.2500 | 50 | 36 |
| 0.1250 | 0.1250 | 50 | 20 |
| 0.2500 | 0.2500 | 90 | 76 |
| 0.1250 | 0.0625 | 50 | 20 |
| 0.0625 | 0.2500 | 50 | 20 |

TABLE B8.5

| Compound A-1.1 ppm | Bixafen ppm | % activity | expected action (Colby) |
|---|---|---|---|
| 0.0313 | | 70 | |
| 0.0156 | | 20 | |
| 0.0078 | | 0 | |
| 0.0039 | | 0 | |
| | 0.0313 | 70 | |
| | 0.0156 | 20 | |
| | 0.0078 | 0 | |
| | 0.0039 | 0 | |
| 0.0313 | 0.0156 | 90 | 76 |
| 0.0156 | 0.0313 | 90 | 76 |
| 0.0156 | 0.0156 | 70 | 36 |
| 0.0156 | 0.0078 | 50 | 20 |
| 0.0156 | 0.0039 | 50 | 20 |
| 0.0078 | 0.0156 | 50 | 20 |
| 0.0039 | 0.0156 | 50 | 20 |

TABLE B8.6

| Compound A-1.2 ppm | Fluopyram ppm | % activity | expected action (Colby) |
|---|---|---|---|
| 0.2500 | | 50 | |
| 0.1250 | | 20 | |
| | 0.2500 | 20 | |
| | 0.1250 | 20 | |
| | 0.0625 | 0 | |
| | 0.0313 | 0 | |
| 0.2500 | 0.2500 | 90 | 60 |
| 0.2500 | 0.1250 | 90 | 60 |
| 0.2500 | 0.0625 | 90 | 50 |
| 0.1250 | 0.2500 | 70 | 36 |
| 0.1250 | 0.1250 | 50 | 36 |
| 0.1250 | 0.0625 | 50 | 20 |
| 0.1250 | 0.0313 | 70 | 20 |

Example B9

Fungicidal Action Against *Monographella nivalis* (Syn. *Microdochium nivale, Fusarium nivale*), Snow Mould, Foot Rot of Cereals Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is evaluated after 4 days. The results are given in Tables B9:

Tables B9: Fungicidal Action Against *Monographella nivalis*:

TABLE B9.1

| Compound A-1.1 ppm | Fenpropimorph ppm | % activity | expected action (Colby) |
|---|---|---|---|
| 0.1250 | | 90 | |
| 0.0625 | | 50 | |
| | 0.5000 | 0 | |
| | 0.2500 | 0 | |
| | 0.1250 | 0 | |
| | 0.0625 | 0 | |
| 0.1250 | 0.5000 | 100 | 90 |
| 0.1250 | 0.2500 | 100 | 90 |
| 0.1250 | 0.1250 | 100 | 90 |
| 0.0625 | 0.2500 | 70 | 50 |
| 0.0625 | 0.1250 | 70 | 50 |
| 0.0625 | 0.0625 | 70 | 50 |

TABLE B9.2

| Compound A-1.2 ppm | Fenpropimorph ppm | % activity | expected action (Colby) |
|---|---|---|---|
| 2.0000 | | 70 | |
| 1.0000 | | 50 | |
| | 2.0000 | 0 | |
| | 1.0000 | 0 | |
| | 0.5000 | 0 | |
| 2.0000 | 2.0000 | 100 | 70 |
| 2.0000 | 1.0000 | 90 | 70 |
| 2.0000 | 0.5000 | 90 | 70 |
| 1.0000 | 2.0000 | 90 | 50 |
| 1.0000 | 1.0000 | 70 | 50 |

TABLE B9.3

| Compound A-1.1 ppm | Bixafen ppm | % activity | expected action (Colby) |
|---|---|---|---|
| 0.0625 | | 50 | |
| 0.0313 | | 20 | |
| | 0.2500 | 20 | |
| | 0.1250 | 0 | |
| | 0.0625 | 0 | |
| | 0.0313 | 0 | |
| 0.0625 | 0.2500 | 90 | 60 |
| 0.0625 | 0.1250 | 90 | 50 |
| 0.0625 | 0.0625 | 70 | 50 |
| 0.0625 | 0.0313 | 70 | 50 |
| 0.0313 | 0.1250 | 50 | 20 |
| 0.0313 | 0.0625 | 50 | 20 |

Example B10

Fungicidal Action Against *Colletotrichum lagenarium* (Syn. *Glomerella lagenarium*), Anthracnose of Cucurbits Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is evaluated after 3 days. The results are given in Tables B10:

Tables B10: Fungicidal Action Against *Colletotrichum lagenarium*:

TABLE B10.1

| Compound A-1.2 ppm | Fenpropimorph ppm | % activity | expected action (Colby) |
|---|---|---|---|
| 1.0000 | | 50 | |
| 0.5000 | | 20 | |
| | 2.0000 | 20 | |
| | 1.0000 | 20 | |
| | 0.5000 | 0 | |
| | 0.2500 | 0 | |
| 1.0000 | 2.0000 | 70 | 60 |
| 1.0000 | 1.0000 | 70 | 60 |
| 1.0000 | 0.5000 | 70 | 50 |
| 1.0000 | 0.2500 | 70 | 50 |
| 0.5000 | 2.0000 | 50 | 36 |

TABLE B10.2

| Compound A-1.2 ppm | Ipconazole ppm | % activity | expected action (Colby) |
|---|---|---|---|
| 0.5000 | | 20 | |
| 0.1250 | | 0 | |
| 0.0625 | | 0 | |
| 0.0313 | | 0 | |
| | 0.1250 | 20 | |
| 0.5000 | 0.1250 | 50 | 36 |
| 0.1250 | 0.1250 | 50 | 20 |
| 0.0625 | 0.1250 | 50 | 20 |
| 0.0313 | 0.1250 | 50 | 20 |

What is claimed is:

1. A composition suitable for control of diseases caused by phytopathogens comprising a synergistically effective amount of (A) a compound of formula I

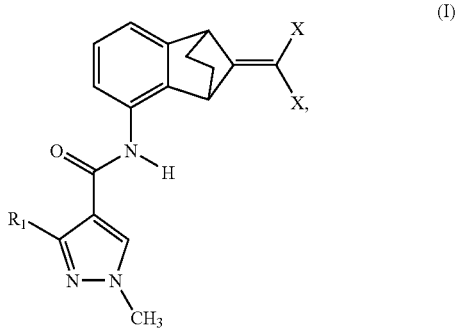

wherein $R_1$ is difluoromethyl or trifluoromethyl and X is chloro, fluoro or bromo; and (B1) a strobilurin fungicide.

2. A composition according to claim 1, wherein component (B1) is a fungicide selected from the group consisting of azoxystrobin, fluoxastrobin, picoxystrobin, pyraclostrobin, and trifloxystrobin.

3. A composition according to claim 1, wherein component (B1) is a fungicide selected from the group consisting of azoxystrobin, fluoxastrobin, picoxystrobin, and pyraclostrobin.

4. A composition according to claim 1, wherein component (A) is 3-difluoromethyl-1-methyl-1H-pyrazole-4-carboxylic acid (9-dichloromethylidene-benzonorbornene-5-yl)amide and component (B1) is selected from the group consisting of azoxystrobin and picoxystrobin.

5. A composition according to claim 1, wherein component (A) is 3-difluoromethyl-1-methyl-1H-pyrazole-4-carboxylic acid (9-difluoromethylidene-benzonorbornene-5-yl)amide and component (B1) is azoxystrobin.

6. A composition according to claim 1, wherein the weight ratio of (A) to (B1) is from 2000:1 to 1:1000.

7. A composition according to claim 1, wherein component (A) is 3-difluoromethyl-1-methyl-1H-pyrazole-4-carboxylic acid (9-dichloromethylidene-benzonorbornene-5-yl)amide.

8. A method of controlling diseases on useful plants or on propagation material thereof caused by phytopathogens, which comprises applying to the useful plants, the locus thereof or propagation material thereof a composition according to claim 1.

9. A method of controlling diseases on soybean plants caused by phytopathogens, which comprises applying to the soybean plants or to the locus thereof a composition according to claim 1.

10. A method according to claim 9, wherein the phytopathogen is *Phakopsora pachyrhizi*.

11. A method according to claim 10, wherein the soybean plants are glyphosate tolerant and wherein the composition further comprises glyphosate.

12. A method according to claim 10, wherein the composition is applied to the soybean plants or the locus thereof.

* * * * *